United States Patent
Weihe et al.

(10) Patent No.: US 11,090,082 B2
(45) Date of Patent: Aug. 17, 2021

(54) COLPOTOMY SYSTEMS, DEVICES, AND METHODS WITH ROTATIONAL CUTTING

(71) Applicant: COVIDIEN LP, Mansfield, MA (US)

(72) Inventors: Jason G. Weihe, Longmont, CO (US); James D. Allen, IV, Broomfield, CO (US); Ansel Dow, Eugene, OR (US); Thomas E. Drochner, Longmont, CO (US); Stuart R. Hart, Tampa, FL (US); Michael B. Lyons, Boulder, CO (US); Scott J. Prior, Shelton, CT (US); John R. Twomey, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 691 days.

(21) Appl. No.: 15/593,387

(22) Filed: May 12, 2017

(65) Prior Publication Data
US 2018/0325552 A1    Nov. 15, 2018

(51) Int. Cl.
*A61B 18/12*    (2006.01)
*A61B 18/14*    (2006.01)
(Continued)

(52) U.S. Cl.
CPC ........ *A61B 17/42* (2013.01); *A61B 17/32002* (2013.01); *A61B 18/1482* (2013.01); *A61B 18/1485* (2013.01); *A61B 17/4241* (2013.01); *A61B 90/30* (2016.02); *A61B 2017/00287* (2013.01); *A61B 2017/00477* (2013.01); *A61B 2017/00557* (2013.01); *A61B 2017/00876* (2013.01); *A61B 2017/320052* (2013.01); *A61B 2017/4216* (2013.01); *A61B 2017/4225* (2013.01); *A61B 2018/0022* (2013.01); *A61B 2018/00285* (2013.01);
(Continued)

(58) Field of Classification Search
CPC combination set(s) only.
See application file for complete search history.

(56) References Cited

U.S. PATENT DOCUMENTS

| 4,597,030 A | 6/1986 | Brody et al. |
| 4,804,240 A | 2/1989 | Mori |

(Continued)

FOREIGN PATENT DOCUMENTS

| CN | 202489982 U | 10/2012 |
| CN | 202920313 U | 5/2013 |

(Continued)

OTHER PUBLICATIONS

Partial European Search Report issued in European Application No. 18171770.3 dated Sep. 25, 2018.
(Continued)

*Primary Examiner* — Daniel W Fowler
*Assistant Examiner* — Tigist S Demie
(74) *Attorney, Agent, or Firm* — Carter, DeLuca & Farrell LLP

(57) ABSTRACT

A colpotomy system includes a colpotomy cup that extends to a distal surface and defines a longitudinal axis. The colpotomy system further includes a cutter operably coupled to the colpotomy cup and configured to travel along an arcuate path defined about the distal surface of the colpotomy cup. The cutter actuatable to separate a uterus from a vagina as the cutter rotates about the longitudinal axis of the colpotomy cup.

21 Claims, 18 Drawing Sheets

(51) Int. Cl.
  *A61B 17/42* (2006.01)
  *A61B 17/32* (2006.01)
  *A61B 18/00* (2006.01)
  *A61B 17/00* (2006.01)
  *A61B 90/00* (2016.01)
  *A61B 90/30* (2016.01)

(52) U.S. Cl.
  CPC .............. *A61B 2018/00291* (2013.01); *A61B 2018/00559* (2013.01); *A61B 2018/00601* (2013.01); *A61B 2018/141* (2013.01); *A61B 2018/1407* (2013.01); *A61B 2018/1422* (2013.01); *A61B 2018/1452* (2013.01); *A61B 2018/1467* (2013.01); *A61B 2018/1475* (2013.01); *A61B 2090/036* (2016.02); *A61B 2090/3945* (2016.02)

(56) References Cited

U.S. PATENT DOCUMENTS

| | | |
|---|---|---|
| 5,209,754 A | 5/1993 | Ahluwalia |
| 5,394,863 A | 3/1995 | Sanford et al. |
| 5,451,221 A | 9/1995 | Cho et al. |
| 5,487,377 A | 1/1996 | Smith et al. |
| 5,520,698 A | 5/1996 | Koh |
| 5,643,285 A | 7/1997 | Rowden et al. |
| 5,840,077 A | 11/1998 | Rowden et al. |
| 6,032,673 A | 3/2000 | Savage et al. |
| 6,129,662 A | 10/2000 | Li et al. |
| 6,423,075 B1 | 7/2002 | Singh et al. |
| 6,516,216 B1 | 2/2003 | Fontenot et al. |
| 8,025,670 B2 | 9/2011 | Sharp et al. |
| 8,128,622 B2 | 3/2012 | Podhajsky et al. |
| 8,192,444 B2 | 6/2012 | Dycus |
| 8,206,357 B2 | 6/2012 | Bettuchi |
| 8,292,901 B2 | 10/2012 | Auerbach et al. |
| 8,298,213 B2 | 10/2012 | Singh |
| 8,323,278 B2 | 12/2012 | Brecheen et al. |
| 8,453,910 B2 | 6/2013 | Bettuchi et al. |
| 8,460,289 B2 | 6/2013 | Sartor |
| 8,528,563 B2 | 9/2013 | Gruber |
| 8,545,513 B2 | 10/2013 | Blair et al. |
| 8,603,105 B2 | 12/2013 | Sauer |
| 8,663,239 B2 | 3/2014 | Hess |
| 8,696,563 B2 | 4/2014 | Williams et al. |
| 8,784,410 B2 | 7/2014 | Dunning |
| 8,939,988 B2 | 1/2015 | Auerbach et al. |
| 9,011,433 B2 | 4/2015 | Batchelor et al. |
| 9,022,927 B2 | 5/2015 | Kleyman |
| 9,033,977 B2 | 5/2015 | Morozov |
| 9,066,724 B2 | 6/2015 | Jenkins |
| 9,101,390 B2 | 8/2015 | Singh et al. |
| 9,144,454 B2 | 9/2015 | Batchelor et al. |
| 9,392,935 B2 | 7/2016 | Adams et al. |
| 2003/0187334 A1 | 10/2003 | Biswas |
| 2005/0085827 A1 | 4/2005 | G. et al. |
| 2006/0271037 A1 | 11/2006 | Maroney et al. |
| 2006/0291195 A1 | 12/2006 | Horrell et al. |
| 2008/0208210 A1 | 8/2008 | Blair et al. |
| 2009/0182329 A1* | 7/2009 | Dycus .................. A61B 18/14 606/48 |
| 2010/0280524 A1 | 11/2010 | Lopez Zepeda |
| 2011/0130769 A1 | 6/2011 | Boebel et al. |
| 2011/0190689 A1 | 8/2011 | Bennett et al. |
| 2012/0016185 A1 | 1/2012 | Sherts et al. |
| 2012/0116416 A1 | 5/2012 | Neff et al. |
| 2012/0143210 A1* | 6/2012 | Brecheen ........... A61B 17/4241 606/119 |
| 2012/0165826 A1 | 6/2012 | Rhemrev-Pieters |
| 2012/0283718 A1 | 11/2012 | Cosmescu |
| 2012/0323079 A1 | 12/2012 | Bakare et al. |
| 2012/0330324 A1 | 12/2012 | Sauer |
| 2013/0066328 A1 | 3/2013 | Singh et al. |
| 2013/0085508 A1 | 4/2013 | Hess |
| 2013/0110126 A1 | 5/2013 | Mujwid |
| 2013/0131459 A1 | 5/2013 | Williams et al. |
| 2014/0012305 A1 | 1/2014 | Horton et al. |
| 2014/0180282 A1 | 6/2014 | Brecheen et al. |
| 2014/0303641 A1 | 10/2014 | Boebel et al. |
| 2014/0358158 A1* | 12/2014 | Einarsson ............... A61B 17/42 606/119 |
| 2015/0005780 A1* | 1/2015 | Einarsson ...... A61B 17/320016 606/119 |
| 2015/0080905 A1 | 3/2015 | Begemann et al. |
| 2015/0127016 A1 | 5/2015 | Sauer |
| 2015/0133923 A1* | 5/2015 | Batchelor .............. A61B 18/14 606/48 |
| 2015/0351621 A1* | 12/2015 | Hill ........................ A61B 1/303 600/249 |
| 2016/0045757 A1 | 2/2016 | Groseth |
| 2016/0074186 A1 | 3/2016 | Sartor et al. |
| 2016/0095649 A1 | 4/2016 | Motai et al. |
| 2016/0100861 A1 | 4/2016 | Parys et al. |
| 2016/0100862 A1 | 4/2016 | Parys |
| 2016/0106463 A1 | 4/2016 | Egle et al. |
| 2016/0120599 A1* | 5/2016 | Amirana ............... A61B 5/6843 606/3 |
| 2016/0270845 A1* | 9/2016 | Benscoter ........... A61B 18/1492 |

FOREIGN PATENT DOCUMENTS

| | | |
|---|---|---|
| CN | 203244440 U | 10/2013 |
| CN | 203303125 U | 11/2013 |
| CN | 204446045 U | 7/2015 |
| CN | 204698659 U | 10/2015 |
| CN | 205072992 U | 3/2016 |
| DE | 102009018521 A1 | 10/2010 |
| EP | 0865760 | 9/1998 |
| EP | 2243437 A1 | 10/2010 |
| EP | 3068323 A1 | 9/2016 |
| WO | 03/015643 A2 | 2/2003 |
| WO | 2008/136024 A1 | 11/2008 |
| WO | 2011140604 A1 | 11/2011 |
| WO | 2012151622 A1 | 11/2012 |
| WO | 2013/090909 A1 | 6/2013 |
| WO | 2015073147 A1 | 5/2015 |
| WO | 2016/025132 A1 | 2/2016 |

OTHER PUBLICATIONS

Extended European Search Report issued in European Application No. 18171770.3 dated Jan. 25, 2019, 13 pages.

* cited by examiner

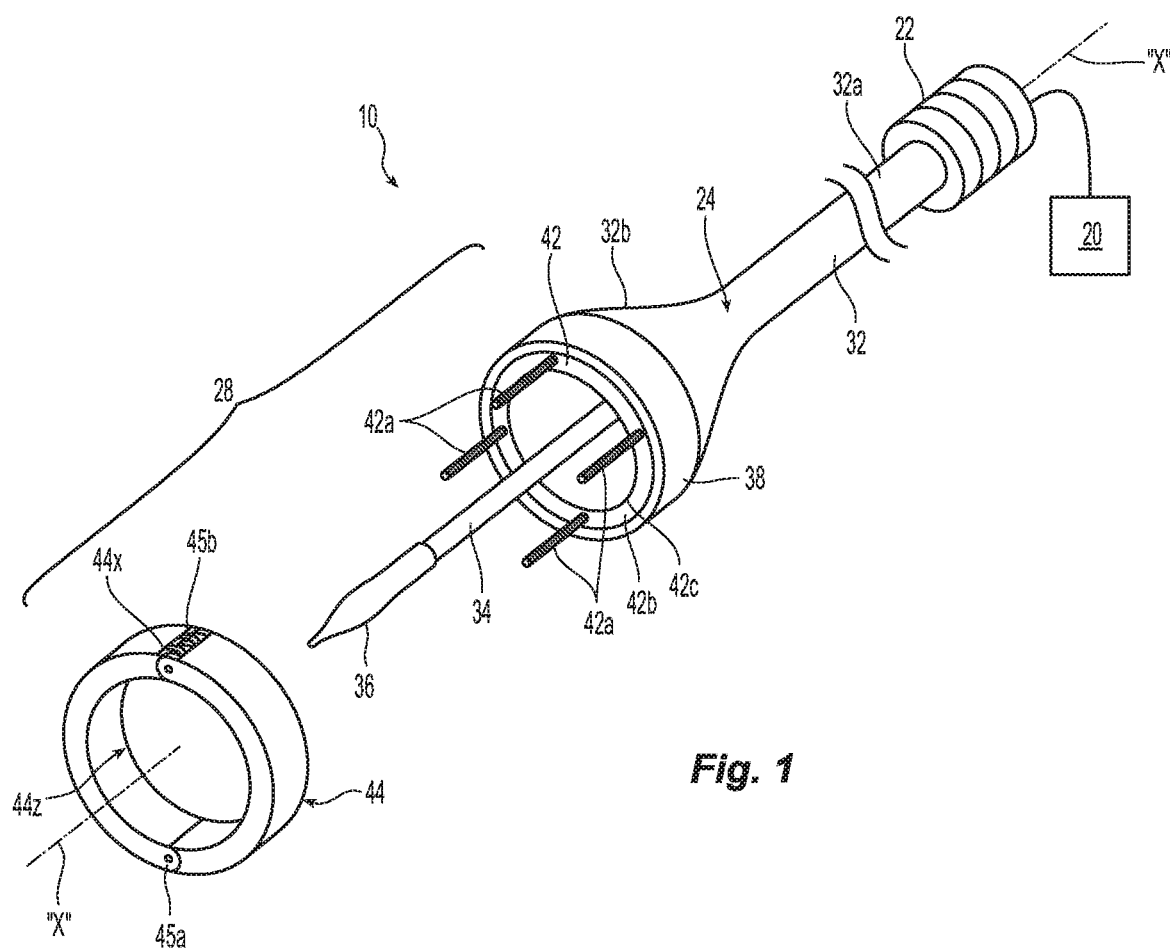
*Fig. 1*
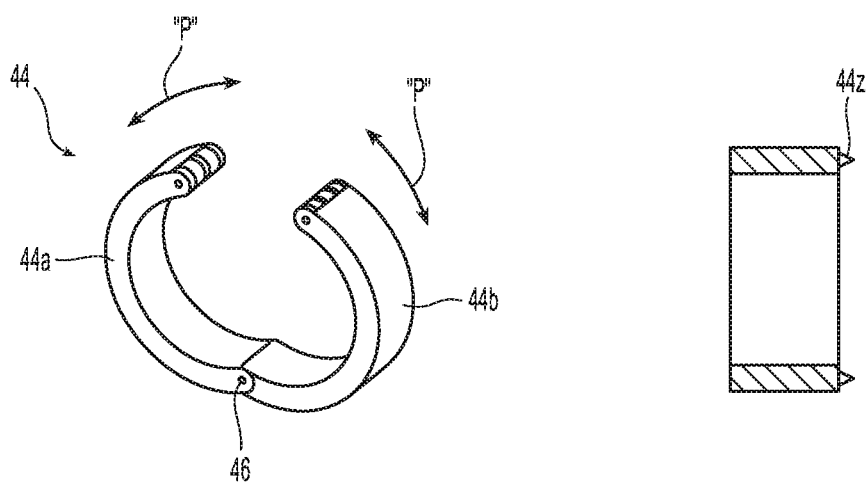
*Fig. 2A*  *Fig. 2B*

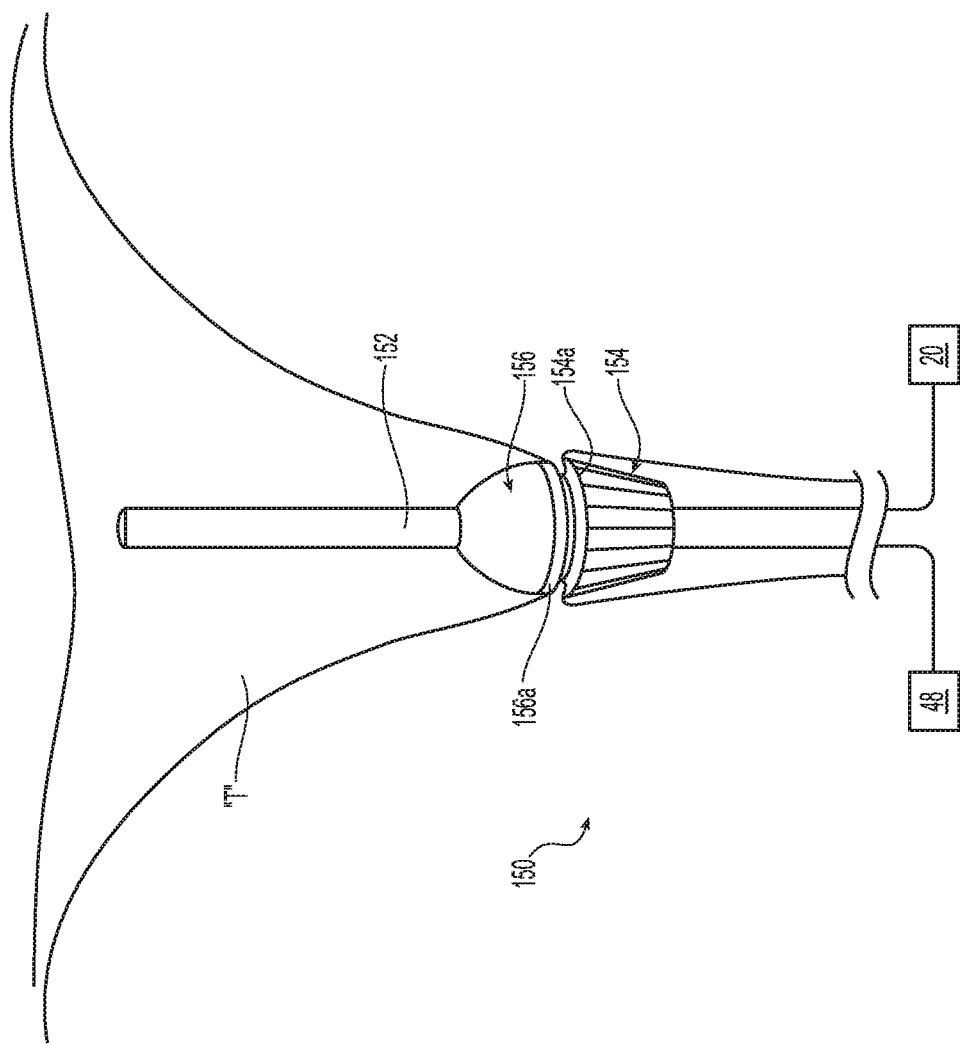

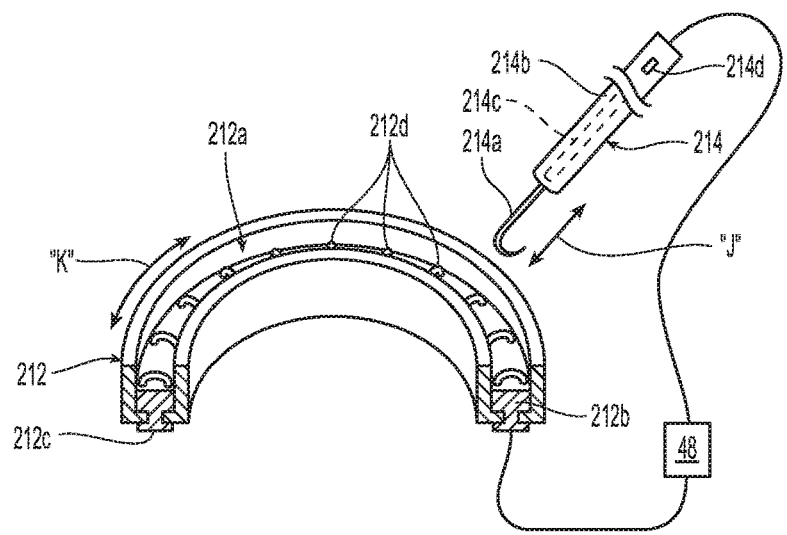
*Fig. 16*
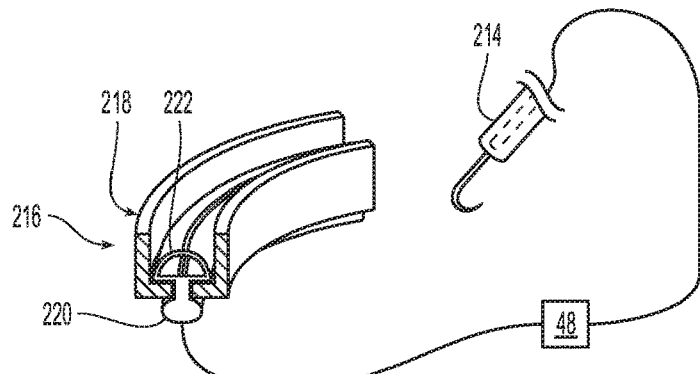
*Fig. 17*
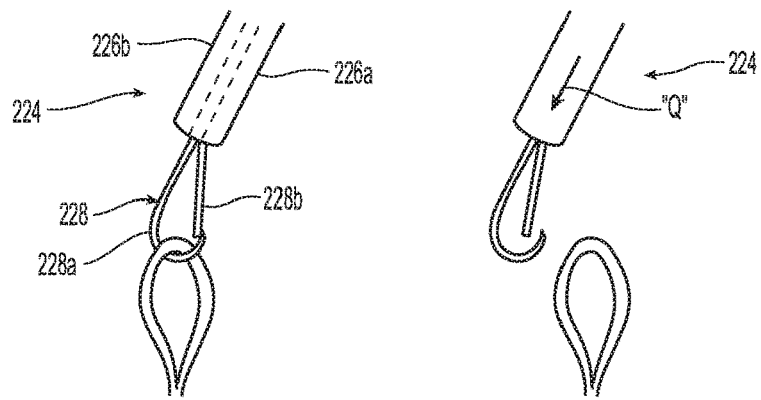
*Fig. 18A*  *Fig. 18B*

COLPOTOMY SYSTEMS, DEVICES, AND METHODS WITH ROTATIONAL CUTTING

TECHNICAL FIELD

The present disclosure relates to laparoscopic hysterectomy and, more particularly, to systems, devices, and methods for performing a colpotomy procedure.

BACKGROUND

Colpotomy, one of the final steps in a laparoscopic hysterectomy, requires making a circular incision in vaginal tissue to separate the uterus from the vagina. This incision is typically performed with the aid of a uterine manipulator.

Uterine manipulators are conventionally used during laparoscopic hysterectomy procedures to mobilize and position the vagina and the cervix to facilitate separation and to enable removal of the uterus or other tissue specimens subsequent to performance of a colpotomy. Typically, uterine manipulators include a handle, a shaft extending distally from the handle, an inflatable balloon supported on the end of the shaft opposite the handle, and a cervical or colpotomy cup supported on the shaft proximally of the inflatable balloon. In use, the inflatable balloon is advanced through the vagina and cervix and is positioned within the uterus in a deflated position. Once positioned within the uterus, the inflatable balloon is inflated to secure the uterine manipulator within the uterus and the colpotomy cup is positioned about the cervix for effectuating the colpotomy.

To effectuate the colpotomy, the clinician is required to identify the in vivo location of the colpotomy cup and position a cutting tool, such as a surgical electrode instrument, so that it can be tracked around the circumference of the colpotomy cup. The insertion angle of the cutting tool, the small target area, and the lack of visual reference points often prevent clinicians from making a clean track and/or incision.

SUMMARY

Accordingly, a need exists to provide systems, devices, and/or methods for improving colpotomy procedures.

In accordance with an aspect of the present disclosure, a colpotomy system includes a colpotomy cup and a cutter. The colpotomy cup extends to a distal surface and defines a longitudinal axis. The cutter is operably coupled to the colpotomy cup and is configured to travel along an arcuate path defined about the distal surface of the colpotomy cup. The cutter is actuatable to separate a uterus from a vagina as the cutter at least partially rotates about the longitudinal axis of the colpotomy cup.

In some embodiments, the colpotomy cup may include a first tube and a second tube. The cutter may be coupled to the first tube such that the cutter rotates with the first tube about the longitudinal axis and relative to the second tube. The first tube may be an inner tube and the second tube may be an outer tube positioned about the inner tube.

The first tube may include a first treating surface and a second treating surface in opposed relation to the first treating surface. The first and second treating surfaces may be adapted to couple to an electrosurgical energy source and configured to treat tissue disposed between the first and second treating surfaces upon activation of the first and second treating surfaces.

In certain embodiment, the cutter may include a cutting surface configured to conduct energy therethrough. The cutter may be coupled to an electrosurgical energy source configured to transmit electrosurgical energy to the cutting surface. The cutting surface may be configured to conduct monopolar energy, bipolar energy, or combinations thereof. The colpotomy cup may include a buffer that prevents the cutting surface from directly contacting tissue.

In some embodiments, the cutter may include one or more light emitting diodes configured to facilitate in vivo positioning of the cutter when illuminated.

In certain embodiments, the cutter may include a bipolar wheel configured to treat tissue.

In some embodiments, the cutter may include first and second electrodes. The first electrode may be supported by a first material having a first magnetic polarity. The second electrode may be supported by a second material having a second magnetic polarity. The magnetic polarities of the first and second materials may be configured to maintain the first and second electrodes in opposing relation during cutting. The first and second electrodes may be bipolar and configured to sever tissue as the cutter encircles the distal surface of the colpotomy cup.

In certain embodiments, the colpotomy system may further include a central shaft extending distally from the colpotomy cup and supporting an inflatable balloon. The cutter may include a first electrode coupled to the distal surface of the colpotomy cup and a second electrode coupled to a proximal surface of the inflatable balloon. The inflatable balloon may be configured to maintain the first and second electrodes in relation during cutting.

In some embodiments, the colpotomy cup may be movable between an unexpanded position and an expanded position to facilitate identification of the colpotomy cup in vivo. The colpotomy cup may expand radially as the colpotomy cup moves from the unexpanded position to the expanded position.

In certain embodiments, the cutter may include a movable blade that is actuatable to sever tissue as the cutter rotates about the longitudinal axis.

In some embodiments, the colpotomy cup may include one or more light emitting diodes on the distal surface thereof.

In certain embodiments, the cutter may be movable relative to the colpotomy cup between an undeployed position and a deployed position. The cutter may include a cutting head that is recessed from the distal surface of the colpotomy cup in the undeployed position and that is extended above the distal surface of the colpotomy cup in the deployed position to enable the cutting head to sever tissue adjacent the distal surface of the colpotomy cup. The cutter may be in the form of a cautery spatula.

In some embodiments, the colpotomy system may further include a vacuum source and one or more vacuum conduits in fluid communication with the vacuum source. The vacuum conduits may be defined about the colpotomy cup and configured to apply negative pressure around the colpotomy cup to approximate tissue toward the distal surface of the colpotomy cup and to enable the cutter to sever tissue disposed in proximity to the distal surface of the colpotomy cup.

In some embodiments, the colpotomy system may further include a hooked electrode configured to operably couple to the colpotomy cup and adapted to couple to an electrosurgical energy source configured to transmit electrosurgical energy to the hooked electrode. The colpotomy cup may include one or more loops configured to engage the hooked electrode. The hooked electrode may be configured to rotate with the one or more loops around the longitudinal axis of the colpotomy cup relative to the distal surface of the colpotomy cup.

In certain embodiments, the cutter may include a hooked electrode and the colpotomy cup may include an inner lip, an outer lip, or combinations thereof. The hooked electrode may be configured to track along one of the inner lip, the outer lip, or combinations thereof to sever tissue disposed about the distal surface of the colpotomy cup.

According to another an aspect of the present disclosure, a colpotomy system, includes a colpotomy cup and a cutter. The colpotomy cup defines a longitudinal axis. The cutter is operably coupled to the colpotomy cup and includes an inner jaw member and an outer jaw member. One or both of the inner or outer jaw members may movable toward the other of a respective one of the inner or outer jaw members to capture vaginal tissue between the inner and outer jaw members and incise the captured vaginal tissue along an arcuate path defined about the colpotomy cup to separate a uterus from a vagina.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein:

FIG. 1 is a perspective view of one embodiment of a colpotomy system in accordance with the present disclosure with an outer jaw member of the colpotomy system separated from the colpotomy system and shown in a closed position;

FIG. 2A is a perspective view of the outer jaw member of FIG. 1 shown in an open position;

FIG. 2B is a side, longitudinal, cross-sectional view of another embodiment of an outer jaw member;

FIG. 9 is a side view of a distal portion of yet another embodiment of a colpotomy system positioned in vivo;

FIG. 16 is a perspective view, in partial cross-section, of yet another embodiment of a colpotomy system;

FIG. 17 is a perspective view, in partial cross-section, of a portion of another embodiment of a colpotomy system;

FIGS. 18A and 18B are progressive views illustrating an embodiment of an electrode instrument of another embodiment of a colpotomy system coupling to a loop electrode of the colpotomy system;

DETAILED DESCRIPTION

Figure 3:
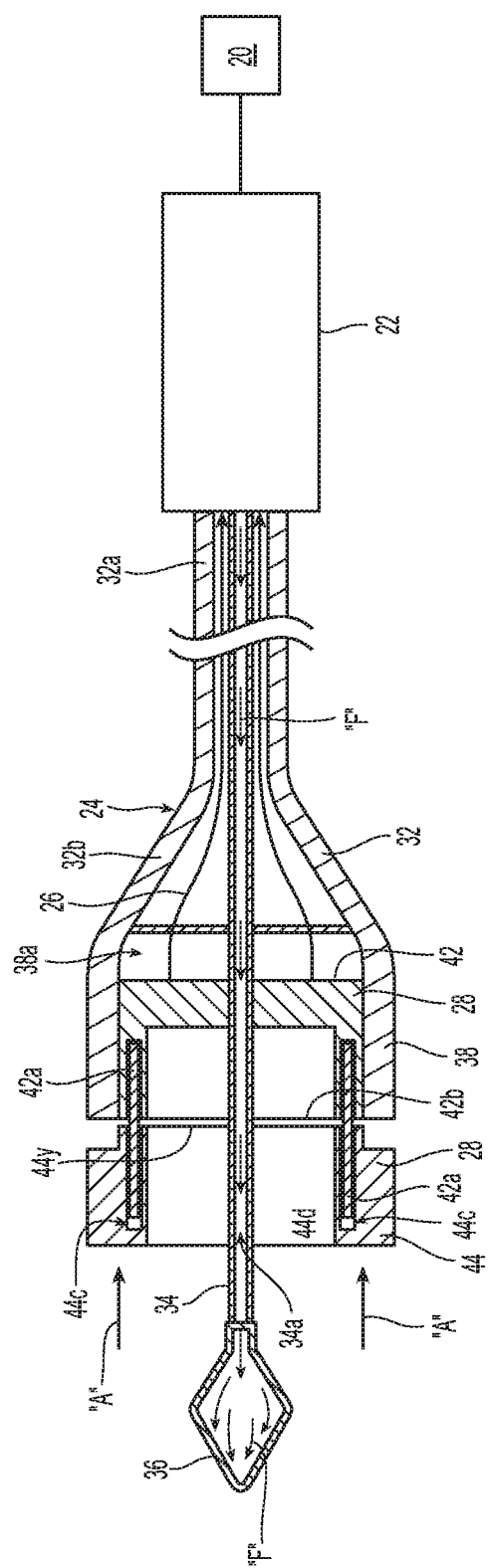
FIG. 3 is a side, longitudinal, cross-sectional view of the colpotomy system of FIG. 1 with the outer jaw member coupled to the colpotomy system.

Embodiments of the present disclosure are described in detail with reference to the drawings, in which like reference numerals designate identical or corresponding elements in each of the several views. As used herein, the term "distal" refers to that portion of structure farther from the user, while the term "proximal" refers to that portion of structure, closer to the user. As used herein, the term "clinician" refers to a doctor, nurse, or other care provider and may include support personnel.

In the following description, well-known functions or constructions are not described in detail to avoid obscuring the present disclosure in unnecessary detail.

Turning now to FIGS. 1-4, one embodiment of a colpotomy system, generally referred to as 10, is shown and may be in the form of a uterine manipulator. Colpotomy system 10 includes an inflation source 20, a handle 22 coupled to inflation source 20, a shaft assembly 24 that extends distally from handle 22 and defines a longitudinal axis "X-X," a drive assembly 26 supported by shaft assembly 24 and coupled to handle 22, and a cutter 28 supported by shaft assembly 24 and coupled to drive assembly 26. Drive assembly 26 can include any suitable mechanical, electrical, and/or electromechanical component configured to impart force (e.g., axial, rotational, or combinations thereof) to cutter 28 (e.g., pneumatic, hydraulic, cables, rods, gears, pulleys, circuits, controllers, wiring, etc.).

Shaft assembly 24 of colpotomy system 10 includes an outer tube 32 having a proximal portion 32a that extends distally from handle 22 of colpotomy system 10, and a distal portion 32b that extends distally from proximal portion 32a of outer tube 32. Distal portion 32b of outer tube 32 forms a colpotomy cup 38 for engaging and/or manipulating vaginal tissue such as a patient's cervix "C." Shaft assembly 24 further includes an inflation shaft 34 that extends distally from handle 22 to an inflatable balloon 36. Inflation shaft 34 of shaft assembly 24 defines a lumen 34a that extends between inflation source 20 and inflatable balloon 36 such that inflation source 20 is in fluid communication with inflatable balloon 36 to selectively inflate inflatable balloon 36 (with inflation fluid "F" such as saline or the like) from a deflated position (FIG. 1) to an inflated position (FIG. 3). In some embodiments, inflation shaft 34, inflatable balloon 36, and/or inflation source 20 are not included in colpotomy system 10.

Colpotomy cup 38 of shaft assembly 24 defines a cutter chamber 38a and supports cutter 28. Cutter 28 includes an inner jaw member 42 movably mounted within cutter chamber 38a of colpotomy cup 38, and an outer jaw member 44 that is selectively attachable to inner jaw member 42. Inner and outer jaw members 42, 44 of cutter 28 may be in the form of a punch and die configuration.

A proximal portion of inner jaw member 42 of cutter 28 is coupled to a distal portion of drive assembly 26 to enable drive assembly 26 to axially move inner jaw member 42 (at least portions thereof) relative to colpotomy cup 38. Inner jaw member 42 further includes coupling rods 42a that extend distally from inner jaw member 42 and are configured to couple to a proximal portion of outer jaw member 44 of cutter 28. Inner jaw member 42 also includes a first cutting surface 42b, which may function as a punch, and which includes a cutting edge 42c.

In some embodiments, the distal portion of drive assembly 26 of colpotomy system 10 can be directly coupled to one or more of coupling rods 42a of inner jaw member 42 to draw and/or pull coupling rods 42a proximally relative to inner jaw member 42 and/or to colpotomy cup 38. In certain embodiments, coupling rods 42a can be threadably coupled to inner jaw member 42 of cutter 28 and movable (e.g., axially and/or rotationally) relative to inner jaw member 42 in response to actuation of drive assembly 26, for example, to approximate inner and outer jaw members 42, 44.

With reference to FIGS. 1 and 2A, outer jaw member 44 of cutter 28 includes flexible arms 44a, 44b that are pivotably coupled together by a pivot pin 46 at one end 45a of flexible arms 44a, 44b and selectively couplable together at another end 45b of flexible arms 44a, 44b by any suitable mechanical connection 44x (e.g., friction fit, magnetics, pin, etc.). In particular, as indicated by arrows "P," flexible arms 44a, 44b of outer jaw member 44 are pivotable to enable outer jaw member 44 to move between an open position (FIG. 2A)(e.g., u-shaped configuration) and a closed position (FIG. 1). In the open position of outer jaw member 44, outer jaw member 44 has a U and/or W-shaped configuration, depending on how far apart flexible arms 44a, 44b of outer jaw member 44 are separated. In the closed position of outer jaw member 44, with opposite ends 45a, 45b of flexible arms 44a, 44b coupled together, outer jaw member 44 defines an O and/or ring-shaped configuration defining a central opening 44z therethrough.

In the open position of outer jaw member 44, flexible arms 44a, 44b of outer jaw member 44, in some embodiments, can be separated in a manner sufficient to enable outer jaw member 44 to be advanced through an access port or trocars (e.g., 5-12 mm cannulas—not shown). For a more detailed description of one example of a surgical access port, reference can be made to U.S. Pat. Nos. 9,022,927 or 8,206,357, the entire contents of each of which are incorporated by reference herein.

Outer jaw member 44 of cutter 28 further includes rod-receiving slots 44c defined in a proximal surface of outer jaw member 44. Rod-receiving slots 44c are configured to receive coupling rods 42a of inner jaw member 42 therein (e.g., via friction fit, threaded-fit or the like). Outer jaw member 44 further includes a second cutting surface 44d that may function as a die (of a punch and die configuration). Second cutting surface 44d of outer jaw member 44 includes a cutting edge 44y that is configured to cooperate with cutting edge 42c of first cutting surface 42b of inner jaw member 42 to sever vaginal tissue captured between inner and outer jaw members 42, 44 of cutter 28.

In some embodiments, first and/or second cutting surfaces 42b, 44d of inner and outer jaw members 42, 44, respectively, may be electrically coupled to an energy source 48, such as an electrosurgical generator (see FIG. 4), to cut and/or treat, e.g., coagulate, seal, etc., tissue positioned between inner and outer jaw members 42, 44 of cutter 28 when energy, such as electrosurgical energy (e.g., monopolar, bipolar, or combinations thereof), is conducted through first and/or second cutting surfaces 42b, 44d of inner and outer jaw members 42, 44.

Although energy source 48 may include any suitable energy source, for a more detailed description of one example of an electrosurgical generator, reference can be made to U.S. Pat. No. 8,784,410, the entire contents of which are incorporated by reference herein.

Briefly, as seen in FIG. 2B, in certain embodiments, outer jaw member 44 of cutter 28 may be in the form of a "rule die" type cutter with one or more sharpened cutting edges 44z projecting proximally from a proximal surface of outer jaw member 44.

With reference again to FIGS. 3 and 4, in use, inflatable balloon 36 of inflation shaft 34 is positioned into a patient's uterine cavity "UC" and inflated by virtue of inflation source 20 (e.g., with saline) to an inflated position (FIG. 3). Such positioning and inflation facilitates placement and/or securement of colpotomy cup 38 of shaft assembly 24 adjacent to the patient's cervix "C" so that coupling rods 42a of inner jaw member 42 of cutter 28 are positioned peripherally (e.g., circumferentially) about the patient's cervix "C." Colpotomy cup 38 can be manipulated, for example, by moving handle 22, to facilitate positioning and/or manipulation of the patient's cervix "C," as desired. While outer jaw member 44 of cutter 28 is in the open position, outer jaw member 44 is positioned about an outer surface of the patient's uterus "U" and repositioned to the closed position of the outer jaw member 44. In the closed position of the outer jaw member 44, rod-receiving slots 44c of outer jaw member 44 can be aligned with coupling rods 42a of inner jaw member 42 so that outer jaw member 44 can be mounted onto inner jaw member 42 to capture tissue "T" to be incised between inner and outer jaw members 42, 44.

With outer jaw member 44 of cutter 28 mounted on inner jaw member 42 of cutter 28, but with inner and outer jaw members 42, 44 partially unapproximated, drive assembly 26 of colpotomy system 10 can be actuated by handle 22 and/or by one or more actuators thereon (e.g. switches, knobs, buttons, etc.—not shown) to cause inner and outer jaw members 42 to incise tissue (e.g., annular incision)

disposed between inner and outer jaw members 42, 44 by axially and/or rotationally moving one or both of inner and outer jaw members 42, 44 relative to colpotomy cup 38. In some embodiments, actuation of drive assembly 26 may cause approximating movement between inner and/or outer jaw members 44 of cutter 28, as indicated by arrows "A." Inner and outer jaw members 42, 44 may mechanically and/or electrically cooperate to effectuate a colpotomy on tissue disposed between inner and outer jaw members 42, 44 to remove the patient's uterus "U" from the patient's vagina "V." In embodiments with electrosurgical energy coupled to cutter 28, electrosurgical energy can be activated from electrosurgical energy source 48 to treat tissue "T" adjacent the incision. In certain embodiments, electrosurgical energy can be actuated simultaneously with movement of inner and/or outer jaw members 42, 44 relative to colpotomy cup 38 and/or one another.

Once the colpotomy procedure is complete, in vivo portions of the colpotomy system 10 (e.g., colpotomy cup, cutter, etc.) can be removed transvaginally (with or without incised tissue). Inflatable balloon 36 of shaft assembly 24 may be deflated before the transvaginal removal of any of the components of the colpotomy system; but in some instances, deflation of inflatable balloon 36 may not be necessary. For example, where the colpotomy procedure removed a sufficient amount of tissue to create an enlarged opening through which the components can be freely passed, deflation of inflatable balloon 36 would not be necessary.

Figure 5:
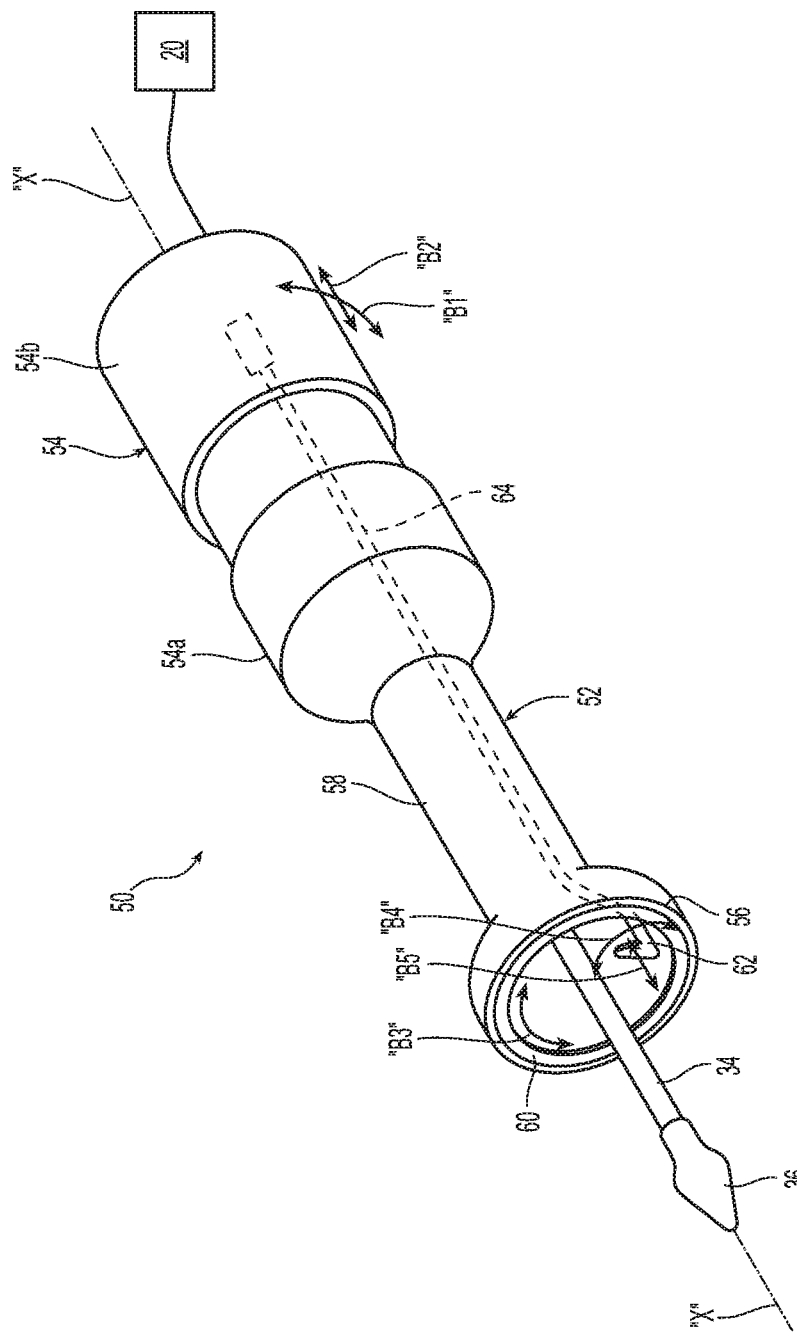
FIG. 5 is a perspective view of another embodiment of a colpotomy system.

Turning now to FIG. 5, another embodiment of a colpotomy system or uterine manipulator, generally referred to as colpotomy system 50 is provided. Colpotomy system 50 defines a longitudinal axis "X-X" and includes a shaft assembly 52 having a handle assembly 54 at a proximal end portion of shaft assembly 52 and an end effector or colpotomy cup 56 at a distal end portion of shaft assembly 52. Handle assembly 54 of shaft assembly 52 includes a stationary portion 54a and a movable portion 54b.

Shaft assembly 52 of colpotomy system 50 includes inflation shaft 34 and inflatable balloon 36 supported on a distal end portion of inflation shaft 34 and in fluid communication with inflation source 20. Shaft assembly 52 further includes an outer tube 58 and an inner tube 60 movably supported within outer tube 58 and operably coupled to movable portion 54b of handle assembly 54. Inner tube 60 of shaft assembly 52 further includes a cutter 62 coupled to a distal end portion of inner tube 60. Cutter 62 is operably coupled to handle assembly 54 by a drive assembly 64 extending through shaft assembly 52.

Movable portion 54b of handle assembly 54 can be configured to move in any suitable manner and/or direction (e.g., axially, rotationally, or combinations thereof) relative to stationary portion 54a of handle assembly 54, as indicated by arrows "B1" and "B2" to operate one or more components of colpotomy system 50 such as inner tube 60 and/or cutter 62. For instance, movement of movable portion 54b relative to stationary portion 54a can be configured to cause inner tube 60 to rotate relative to outer tube 58, as indicated by arrows "B3." Movement of movable portion 54b relative to stationary portion 54a can be configured to cause cutter 62 to actuate or move relative to outer and/or inner tubes 58, 60, as indicated by arrows "B4" and "B5."

Additionally and/or alternatively, handle assembly 54 can include any number of mechanical and/or electrical actuators (not shown) to actuate one or more components of colpotomy system 50. Operation of handle assembly 54, or components thereof, can result, for example, in tissue cutting, inflation, and/or activation of electrosurgical energy.

Figure 4:
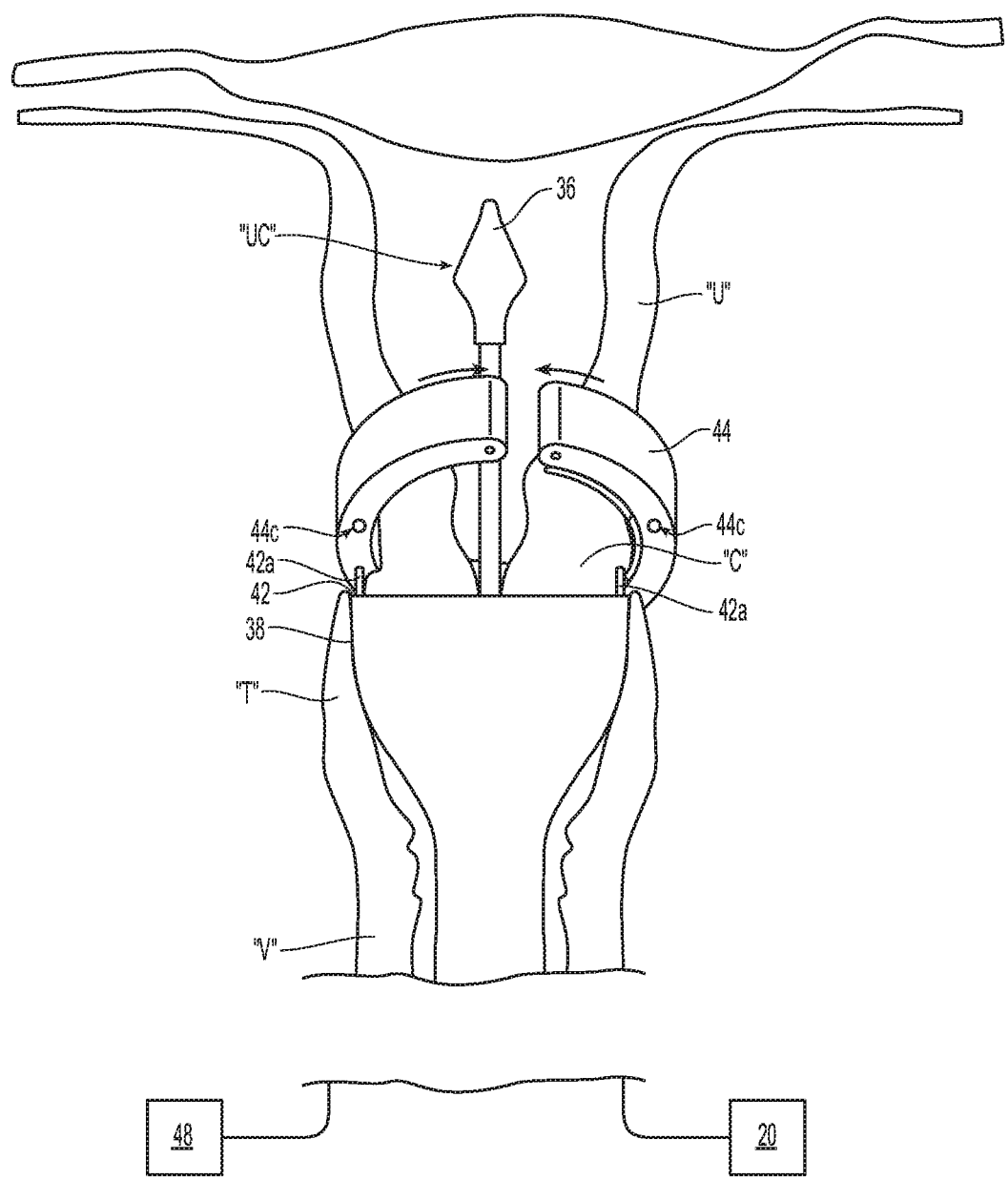
FIG. 4 is a view of the colpotomy system of FIG. 1 positioned in vivo.

Operation of colpotomy system 50 can involve positioning inflatable balloon 36 of shaft assembly 52 into a patient's uterine cavity "UC" (FIG. 4) and inflating inflatable balloon 36 to facilitate placement and/or securement of colpotomy cup 56 of shaft assembly 52 adjacent to the patient's cervix "C" (FIG. 4). Outer tube 58 of shaft assembly 52 can be pressed against intercorporeal or in vivo tissue to enable a clinician to extracorporeally (ex vivo) identify an in vivo location of colpotomy cup 56, for example. Inner tube 60 of shaft assembly 52 can be rotated relative to outer tube 58 of shaft assembly 52, for example, about the longitudinal axis "X-X" of shaft assembly 52 to enable cutter 62 of inner tube 60 to make an annular (e.g., circular) incision in vaginal tissue of the patient to remove the patient's uterus (e.g., a colpotomy).

Cutters, in some embodiments of the presently disclosed colpotomy systems or uterine manipulators, can be actuated and/or activated in conjunction with rotation of inner tube 60 of shaft assembly 52 relative to outer tube 58 of shaft assembly 52 to facilitate annular tissue cutting along an arcuate path for a colpotomy.

Figure 6A:
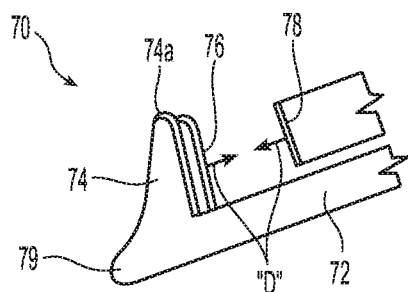
FIGS. 6A-6G are perspective views of various embodiments of cutters of the colpotomy system of FIG. 5.

As seen in FIG. 6A, one embodiment of a cutter, generally referred to as cutter 70, which is configured to rotate with inner tube 60, can include an arm 72 coupled to inner tube 60 (FIG. 5) of shaft assembly 52 of an embodiment of a uterine manipulator or colpotomy system. Arm 70 includes a foot 74 having a treating surface 74a, such as a treating plate, supported on foot 74. Treating surface 74a may be configured to conduct bipolar energy. Arm 60 further includes a first blade 76, which may be stationary and/or movable, and a second blade 78, which is movable relative to first blade 76. Relative movement between first and second blades 76, 78 can be effectuated via actuation handle assembly 54 such that approximating movement between first and second blades 76, 78, as indicated by arrows "D," effectuates tissue cutting. Treating surface 74a, first blade 76, and/or second blade 78 of cutter 70 may be operatively coupled to an electrosurgical energy source, such as electrosurgical generator 48 (FIG. 4), to facilitate cutting and/or treating of tissue. Arm 70 may further include a piercing tip 79 on a distal end portion of arm 70. Piercing tip 79 of arm 70 may include a sharpened cutting edge and/or may be electrically coupled to electrosurgical energy source 48 to effectuate piercing (e.g., monopolar) through tissue to initiate the annular incision for a colpotomy, for example.

Figure 6B:
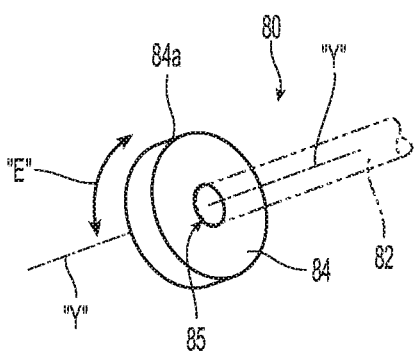

With reference to FIG. 6B, another embodiment of a cutter, generally referred to as cutter 80, is in the form of a wheel operatively coupled to an electrosurgical energy source of an embodiment of a uterine manipulator or colpotomy system. Cutter 80 can include a support shaft 82 and a rotatable wheel 84 rotatably coupled to support shaft 82. As indicated by arrows "E," rotatable wheel 84 is rotatable about a central pivot 85 and/or a transverse axis "Y-Y" defined through central pivot 85 to facilitate cutting and/or treating of tissue as rotatable wheel 84 rotates about transverse axis "Y-Y" (and longitudinal axis "X-X"—FIG. 5).

Rotatable wheel 84 of cutter 80 can be coupled to an electrosurgical energy source (e.g., generator 48) to enable rotatable wheel 84 of cutter 80 to conduct energy (e.g., bipolar, monopolar, or combinations thereof). In some embodiments, cutter 80 includes one or more sharpened cutting edges or blades 84a that facilitate tissue cutting as rotatable wheel 84 of cutter 80 rotates about central pivot 85.

Figure 6C:
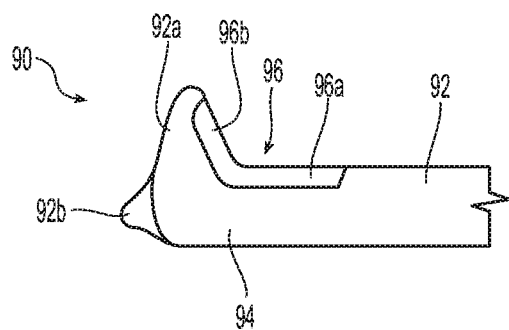

As seen in FIG. 6C, yet another embodiment of a cutter, generally referred to as cutter 90, includes a support shaft 92 having a distal foot 92a and a piercing tip 92b similar to piercing tip 79 of cutter 70. Support shaft 92 of cutter 90 includes an insulated portion 94 (including insulative material) and an electrode portion 96 (including conductive material). Electrode portion 96 of support shaft 92 is operatively coupled to electrosurgical energy (e.g., monopolar) and includes a first segment 96a that extends axially along support shaft 92 and a second segment 96b that extends distally from first segment 96a in a transverse direction along a proximal surface of distal foot 92a of support shaft 92. Electrode portion 96 of support shaft 92 may have a chevron configuration.

Figure 6D:
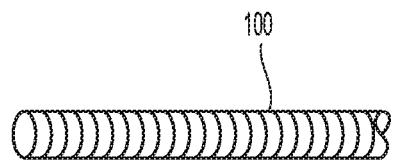
Figure 6E:
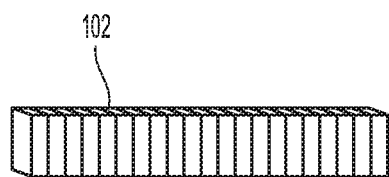

With reference to FIGS. 6D and 6E, other embodiments of cutters, namely, cutters 100, 102, for example, can be in the form of monopolar rods coupled to electrosurgical energy for selectively activating such monopolar rods for cutting and/or treating tissue. For example, as seen in FIG. 6D, cutter 100 is a cylindrical rod, while cutter 102 is a substantially planar rod with a different transverse cross-section than cutter 100. Cutters 100, 102 can include any suitable shape, dimension, and/or cross-section including any circular configuration (e.g., elliptical), any non-circular configuration (e.g., rectilinear), or combinations thereof. In some embodiments, cutters, such as cutter 102, may include one or more sharpened edges to facilitate cutting.

Figure 6F:
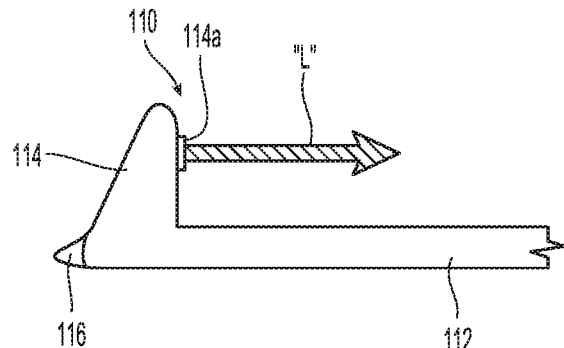

Turning now to FIG. 6F, one embodiment of a cutter, generally referred to as cutter 110, includes a support shaft 112 having a distal foot 114 and a piercing tip 116 extending distally from a distal end portion of support shaft 112. Distal foot 114 includes one or more laser emitters 114a supported on a proximal surface of distal foot 114. Laser emitters 114a are coupled to an energy source (e.g. radio frequency energy) and configured to emit laser energy "L" to cut and/or treat tissue. Laser emitters 114a (e.g., diode, erbium, carbon dioxide, etc.) are configured to emit laser energy at any suitable frequency or wavelength (e.g., between about 2000 nm to about 11000 nm) configured to cut and/or treat, e.g., coagulate and/or seal, tissue. In some embodiments, cutter 110 can include different laser emitters, for example, an erbium laser emitter to cut tissue and a diode laser emitter to treat tissue.

Figure 6G:
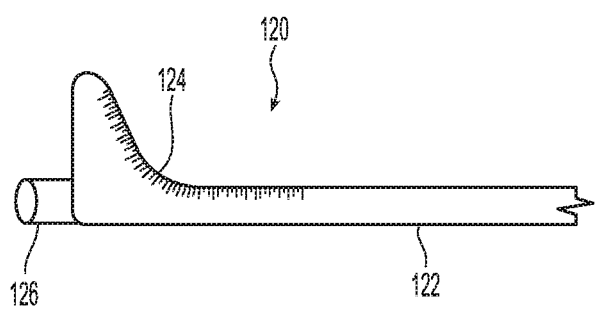

As seen in FIG. 6G, another embodiment of a cutter, generally referred to as cutter 120, includes a support shaft 122 having a sharpened edge 124 to facilitate tissue cutting. Support shaft 122 further includes a light emitting diode 126 supported on a distal end portion of support shaft 122 and configured to emit visible light in a distal direction to facilitate quick and reliable identification of an in vivo cutting location.

Figure 7B:
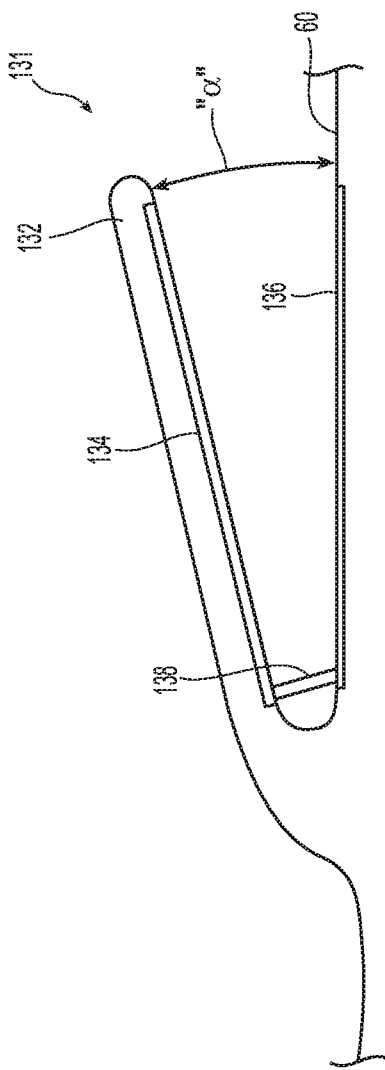
FIG. 7B is an enlarged, side view of the indicated area of detail shown in FIG. 7A.
Figure 7A:
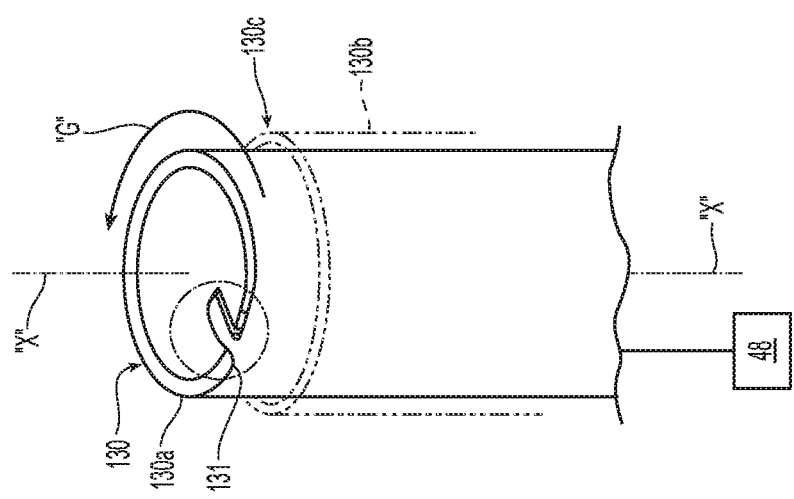
FIG. 7A is a perspective view of a distal portion of one embodiment of a colpotomy system.

Turning now to FIGS. 7A and 7B, still another embodiment of a colpotomy system, generally referred to as colpotomy system 130, is provided. Colpotomy system 130 includes an inner tube 130a and an outer tube 130b that are coupled together to define a colpotomy cup 130c at a distal end portion of inner and outer tubes 130a, 130b. Further, inner and outer tubes 130a, 130b define a longitudinal axis "X-X" therethrough. Inner tube 130a is rotatable relative to outer tube 130b about longitudinal axis "X-X," as indicated by arrow "G," and includes a cutter 131.

Cutter 131 of colpotomy system 130 includes an arm 132 that extends distally from a distal surface of inner tube 130a. Arm 132 of cutter 131 is disposed at an acute angle "α" relative to the distal surface of inner tube 130a. In some embodiments, acute angle "α" ranges between about 1 degree and about 45 degrees. In certain embodiments, acute angle "α" may be up to about 90 degrees.

Cutter 131 of colpotomy system 130 further includes a first treating surface 134 supported on a proximal surface of arm 132 and a second treating surface 136 supported on the distal surface of inner tube 130a. In certain embodiments, first and/or second treating surfaces 134, 136 may be in the form of a treating plate. Second treating surface 136 of cutter 131 is disposed in opposed or mirrored relation to first treating surface 134 of cutter 131. First and second treating surfaces 134, 136 are coupled to an electrosurgical energy source, such as energy source 48, to conduct electrosurgical energy (e.g., bipolar). Cutter 131 further includes a sharpened cutting blade 138 that extends between a proximal surface of arm 132 of cutter 131 and the distal surface of inner tube 130a In use, as inner tube 130a rotates about longitudinal axis "X-X" relative to outer tube 130b, sharpened cutting blade 138 of cutter 131 cuts tissue (e.g., annular incision) as electrosurgical energy conducted through first and second treating surfaces 134, 136 of cutter 131 treat tissue.

Figure 8:
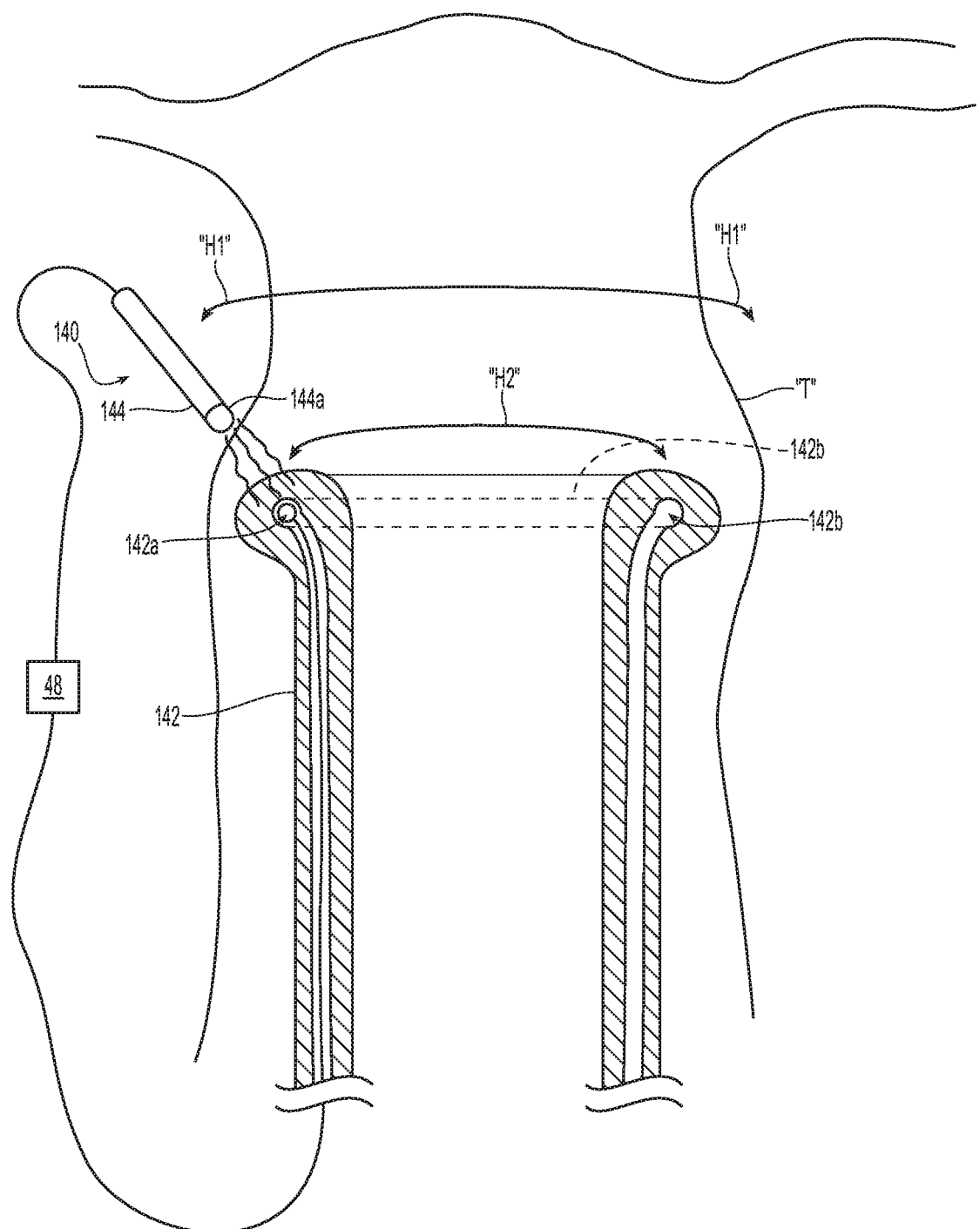
FIG. 8 is a schematic view, in partial cross-section, of a distal portion of another embodiment of a colpotomy system shown positioned in vivo.

With reference to FIG. 8, yet another embodiment of a colpotomy system, generally referred to as colpotomy system 140, is provided. Colpotomy system 140 includes a colpotomy cup 142 and an electrode instrument 144. Colpotomy cup 142 supports an electrode 142a and electrode instrument 144 supports an electrode 144a. Colpotomy cup 142 further defines an annular track 142b through which electrode 142a of colpotomy cup 142 is movable. Electrodes 142a, 144a of colpotomy cup 142 and electrode instrument 144, respectively, are coupled to electrosurgical energy source 48 (e.g., bipolar) and function as a cutter configured to cut and/or treat tissue "T." Each of electrode 142a, 144a of electrode instrument 144 and colpotomy cup 142, respectively, can be supported by one or more materials of electrode instrument 144 or colpotomy cup 142 that have one or more magnetic polarities to enable electrode instrument 144 and colpotomy cup 142 to be magnetically attracted to one another (e.g., opposite polarization). In particular, opposite magnetic polarities of the materials of electrode instrument 144 or colpotomy cup 142 are configured to maintain electrode 142a, 144a in opposing relation during cutting and/or treating of tissue "T" as electrode instrument 144 encircles the distal surface of colpotomy cup 142.

In use, energy source 48 conducts electrosurgical energy through electrodes 142a, 144a of colpotomy cup 142 and electrode instrument 144, respectively, while the magnetic materials of electrode instrument 144 and colpotomy cup 142 maintain a magnetic connection. In particular, rotational movement of electrode instrument 144 about colpotomy cup 142, as indicated by arrows "H1," enables electrode 142a of colpotomy cup 142 to slidably rotate along annular track 142b of colpotomy cup 142, as indicated by arrows "H2," so that electrodes 142a, 144a, which function as a cutter, cooperate to cut and/or treat tissue to effectuate a colpotomy.

Turning now to FIG. 9, yet another embodiment of a colpotomy system, generally referred to as colpotomy system 150, is provided. Colpotomy system 150 includes a central shaft 152 that supports an inflatable balloon 156, and includes a colpotomy cup 154. Inflatable balloon 156 includes a first electrode 156a on a proximal surface of inflatable balloon 156 and colpotomy cup 154 includes a second electrode 154a on a distal surface of colpotomy cup 154. Inflatable balloon 156 may be configured to maintain first and second electrodes 156a, 154a in opposing relation during cutting. First and second electrodes 156a, 154a are coupled to electrosurgical energy source 48 (e.g., bipolar) and inflatable balloon 156 is in fluid communication with inflation source 20.

In use, central shaft 152 is positioned in vivo and inflatable balloon 156 is inflated such that first and second electrodes 156a, 154a are aligned and disposed in proximity to one another. Upon electrical activation of first and/or second electrodes 156a, 154a of inflatable balloon and colpotomy cup 156, respectively, first and/or second electrodes 156a, 154a cooperate to cut and/or coagulate tissue "T" (e.g., annular incision) captured between first and second electrodes 156a, 154a. Although it may not be necessary to rotate either first or second electrodes 156a, 154a to effectuate tissue "T" cutting and/or treating for performing a colpotomy, first and/or second electrodes 156a, 154a can be at least partially rotated, as desired, to facilitate cutting and/or treating of tissue "T." For example, first and/or second electrodes 156a, 154a can be rotated relative to one another by rotating inflatable balloon 156 and/or colpotomy cup 156 relative to one another.

Figure 10A:
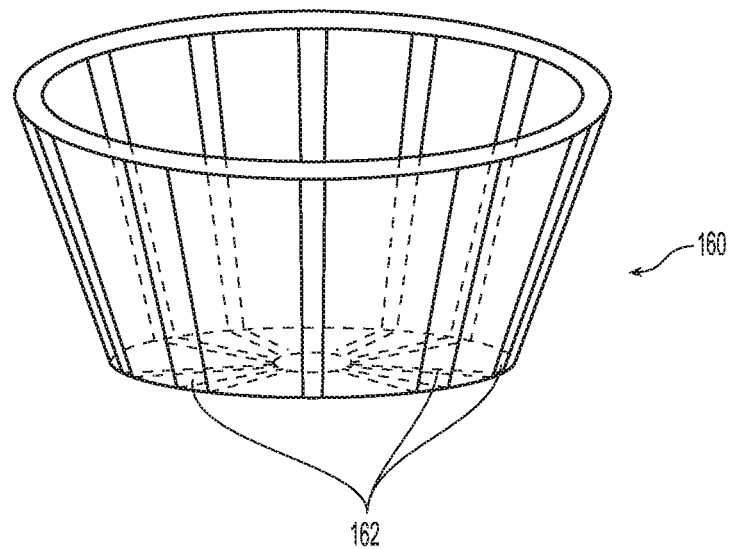
FIG. 10A is a perspective view of one embodiment of a colpotomy cup shown in an unexpanded position.
Figure 10B:
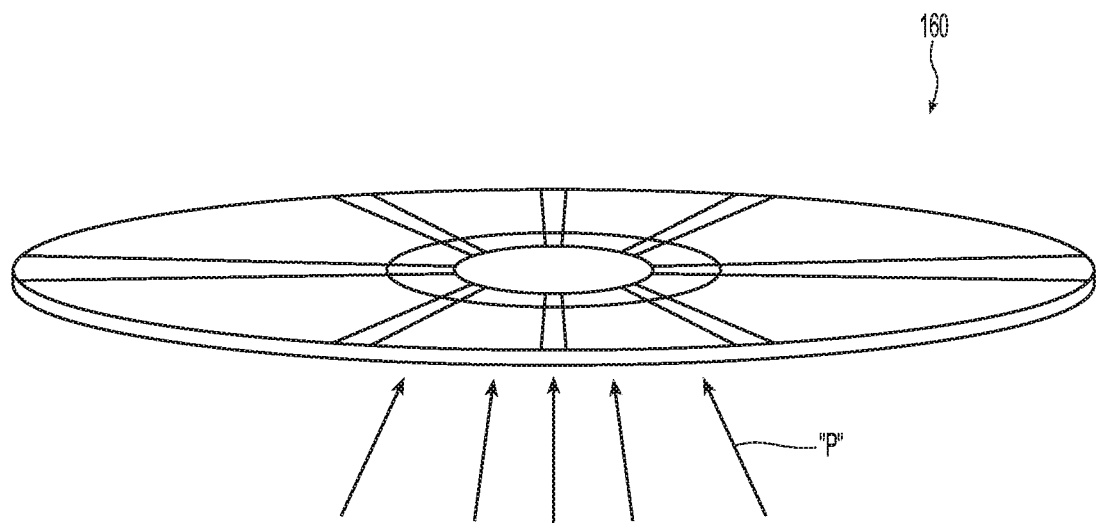
FIG. 10B is a perspective of the colpotomy cup of FIG. 10A shown in an expanded position.

Referring now to FIGS. 10A and 10B, one embodiment of a colpotomy cup, generally referred to as colpotomy cup 160, includes flexible material to enable colpotomy cup 160 to selectively radially expand a diameter of colpotomy cup 160. In particular, colpotomy cup 160 is configured to move between an unexpanded position (FIG. 10A) and an expanded position (FIG. 10B) in response to applied pressure "P."

In the expanded position of colpotomy cup 160, a periphery of colpotomy cup 160 (e.g., an outer diameter of colpotomy cup 160) applies pressure "P" to tissue walls in order to enable increased in vivo position identification of colpotomy cup 160. Removal of applied pressure "P" enables colpotomy cup 160 to move from the expanded position to the unexpanded position. In embodiments, colpotomy cup 160 can include flexible material which enables colpotomy cup 160 to autonomously bias to the unexpanded position upon removal of the applied pressure "P." In some embodiments, colpotomy cup 160 can, at least partially, include shape memory material (e.g., nitinol) to facilitate movement between the unexpanded and expanded positions. In certain embodiments, colpotomy cup 160 includes flexible segments 162, which may be disposed at spaced apart locations about colpotomy cup 160.

Figure 11:
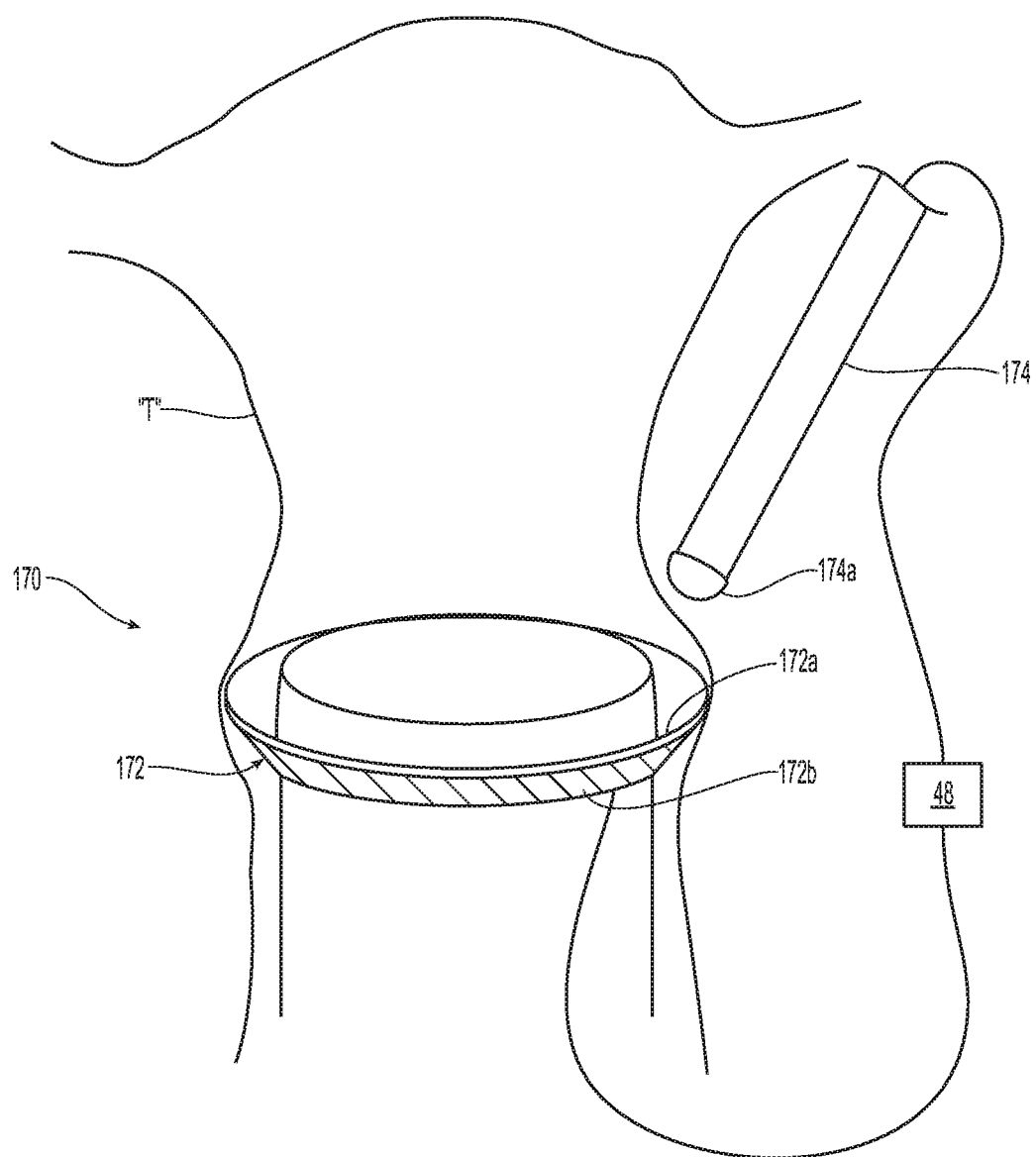
FIG. 11 is a perspective view of a distal portion of yet another embodiment of a colpotomy system positioned in vivo.

As seen in FIG. 11, still another embodiment of a colpotomy system, generally referred to as colpotomy system 170, includes a colpotomy cup 172 and an electrode instrument 174. Colpotomy cup 172 of colpotomy system 170 has a first electrode 172a and a buffer 172b supported adjacent to first electrode 172a. Buffer 172b functions to prevent first electrode 172a from directly contacting tissue "T."

Electrode instrument 174 of colpotomy system 170 has a second electrode 174a that electrically cooperates with first electrode 172a of colpotomy cup 172 to cut and/or coagulate tissue "T." In particular, first and second electrodes 172a, 174a are electrically coupled to an electrosurgical energy source 48 (e.g., bipolar) that is configured to apply electrosurgical energy to first and/or second electrodes 172a, 174a of colpotomy cup 172 and electrode instrument 174, respectively.

Figure 12:
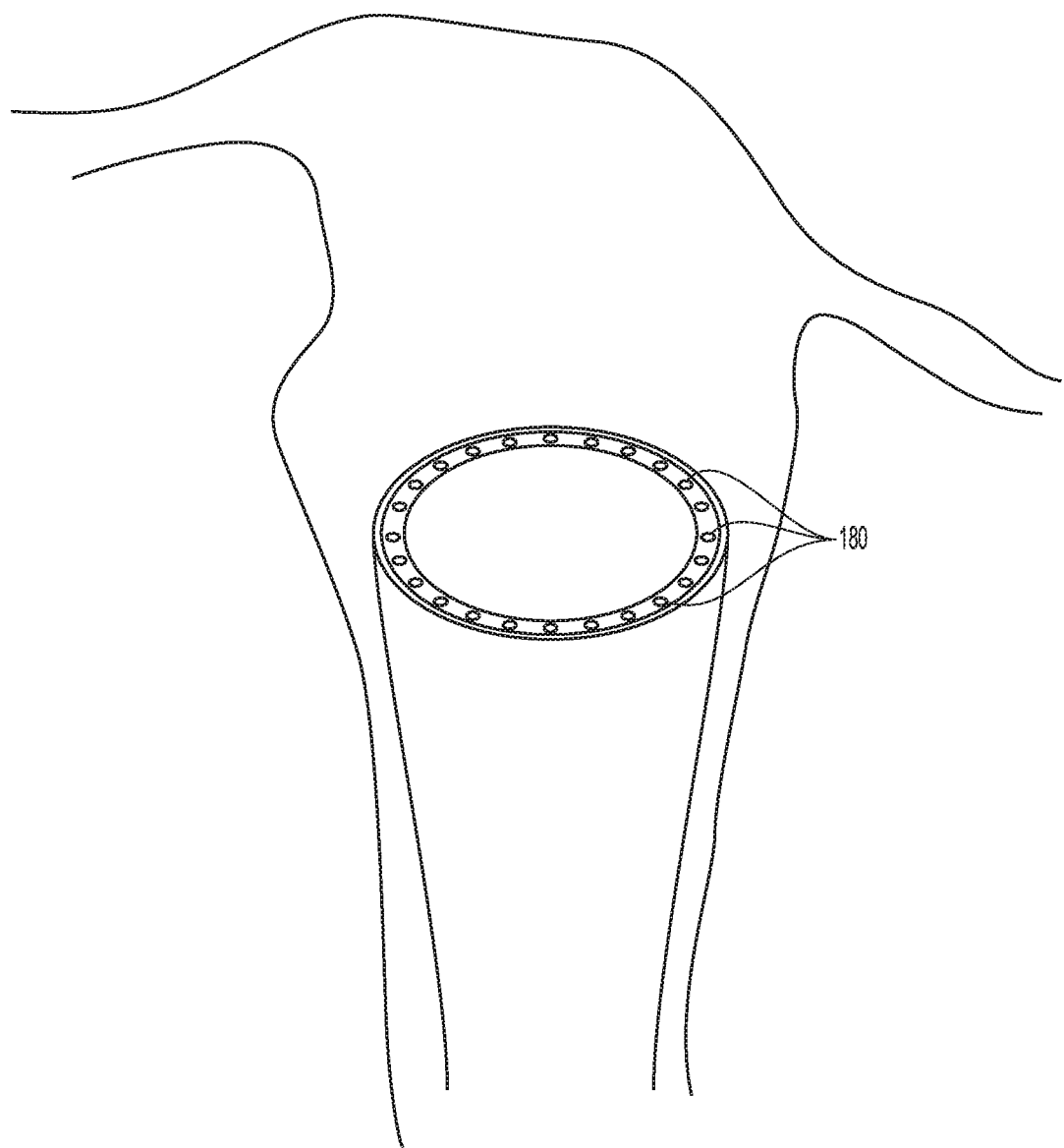
FIG. 12 is a perspective view of a distal portion of one embodiment of colpotomy cup positioned in vivo.

Referring to FIG. 12, some embodiments of the presently disclosed colpotomy cups include a plurality of light emitting diodes 180 supported about a distal end portion of the respective colpotomy cups to facilitate in vivo positioning, guided by light emitted from light emitting diodes 180.

Figure 13A:
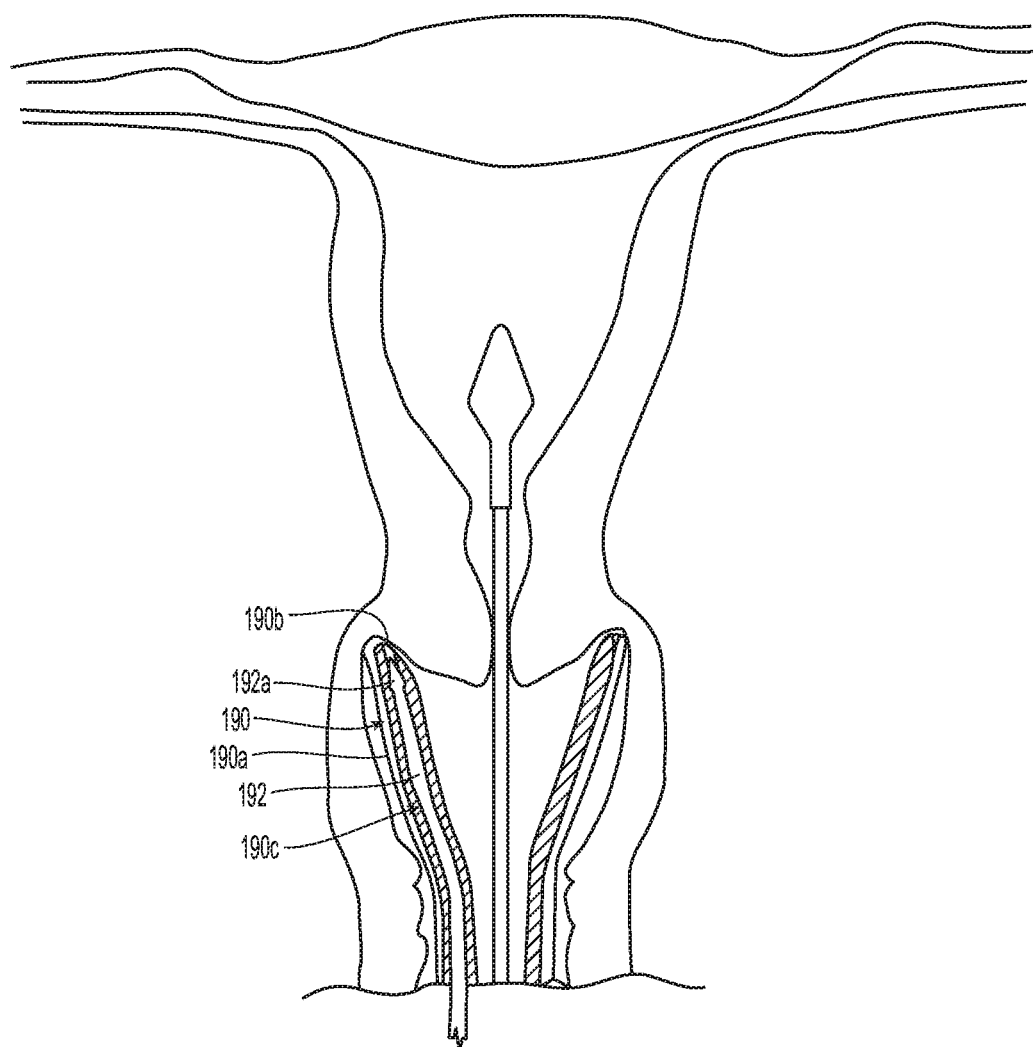
FIG. 13A is a side view, in partial cross-section, of yet another embodiment of a colpotomy system positioned in vivo with a cutter thereof in an undeployed position.
Figure 13B:
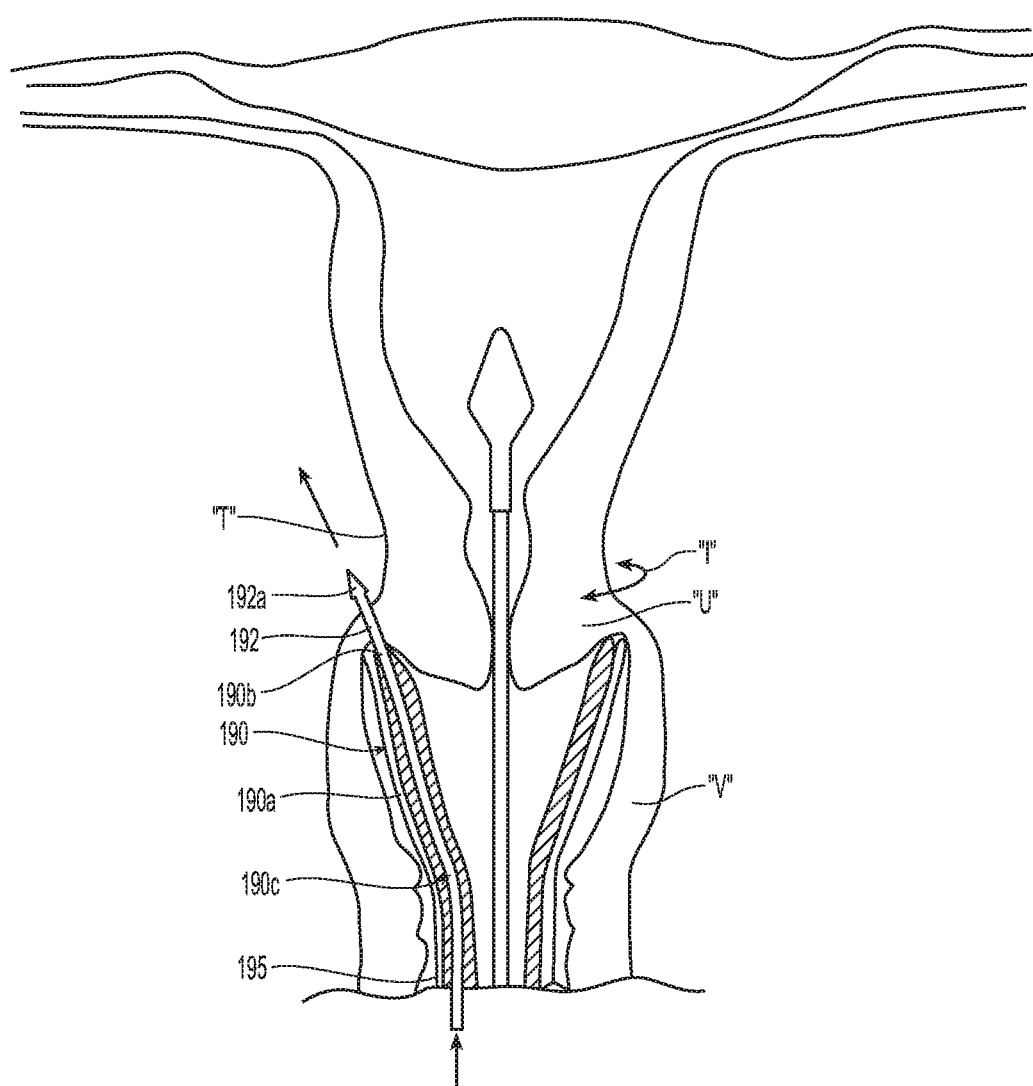
FIG. 13B is a side view, in partial cross-section, of the colpotomy system of FIG. 13A positioned in vivo with the cutter thereof in a deployed position.

Turning now to FIGS. 13A and 13B, certain embodiments of colpotomy systems of the present disclosure include a colpotomy cup 190 having an annular sidewall 190a. Annular side wall 190a extends to a distal end portion 190b and defines a cutter chamber 190c within annular side wall 190a. Cutter chamber 190 of annular side wall 190a supports a deployable cutter 192 that is selectively deployable from cutter chamber 190. Cutter 192 includes a cutting tip 192a and is selectively deployable from a first, undeployed position to a second, deployed position. In the first, undeployed position of cutter 192, cutting tip 192a of cutter 192 is recessed from distal end portion 190b of colpotomy cup 190 and within cutter chamber 190c of annular sidewall 190a (FIG. 13A). In the second, deployed position of cutter 192, cutting tip 192a of cutter 192 is deployed out of cutter chamber 190c of annular sidewall 190a and beyond distal end portion 190b of colpotomy cup 190 (FIG. 13B).

In use, deployable cutter 192 can be deployed at a known "clocking" or predetermined position in tissue such that it can be observed to confirm safe location as it penetrates tissue "T" (e.g., a uterine wall). Once deployable cutter 192 is deployed at the known "clocking" position so that its position can be safely confirmed, deployable cutter 192 can be rotated about the uterus "U," as indicated by arrows "I," to separate the uterus "U" from the vagina "V" (e.g., circular incision). Rotation of deployable cutter 192 can be effectuated by manual and/or motorized rotation of colpotomy cup 190 (and/or one more components of a uterine manipulator 195 to which colpotomy cup 190 may be attached and/or integrally formed).

Figure 14:
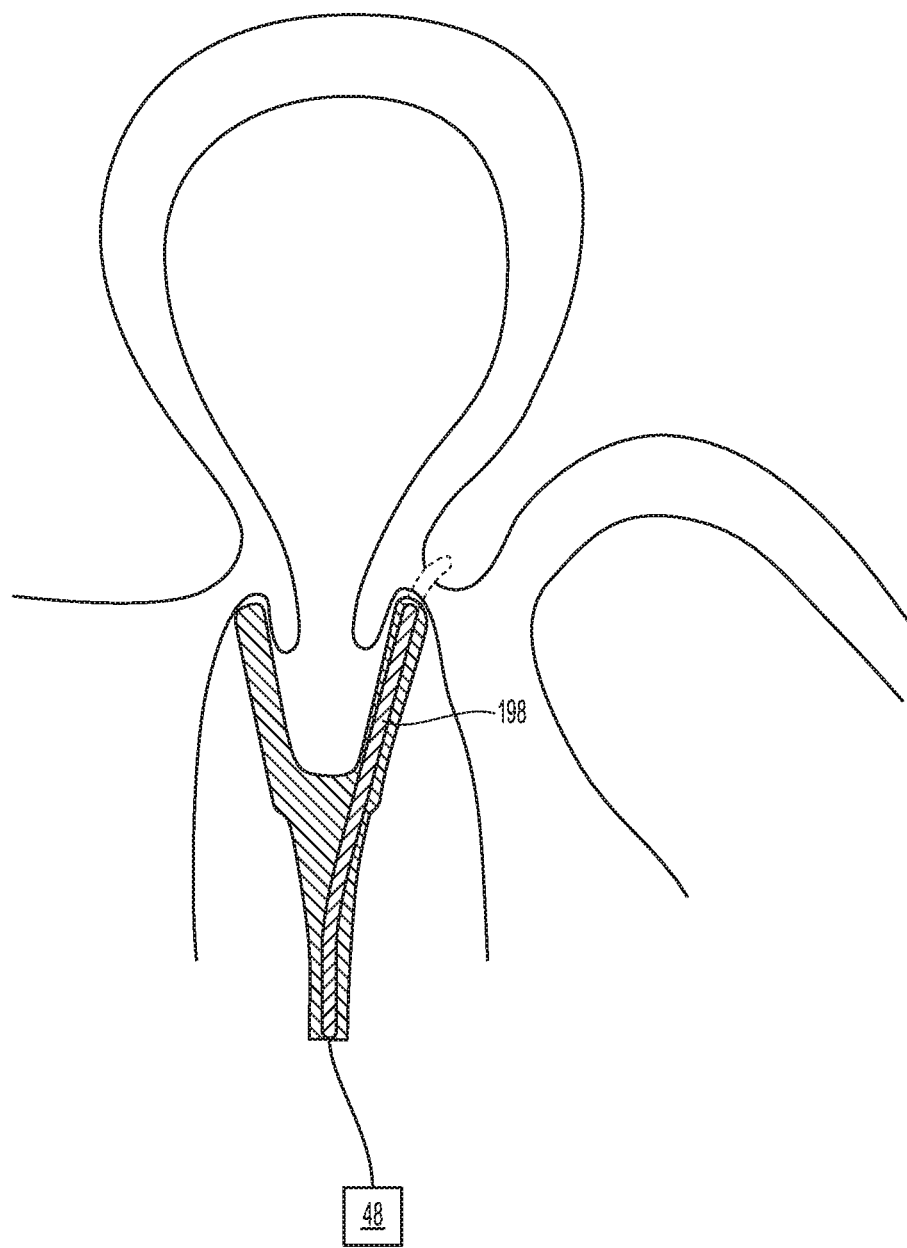
FIG. 14 is a side, longitudinal, cross-sectional view of one embodiment of a colpotomy device shown positioned in vivo.

Briefly, as seen in FIG. 14, cutter 192 can be in the form of an electrocautery blade 198 coupled to electrosurgical energy source 48. Embodiments of electrocautery blade 198 can have any suitable blade configuration (e.g., a spatula, pencil, J-hook, L-hook, etc.). For instance, sample blade configurations can be similar to Medtronic's Cleancoat™ laparoscopic electrode products such as the straight and/or curved spatulas thereof. For a more detailed description of one example of an electrocautery blade, reference can be made to U.S. Pat. No. 8,128,622 or 8,460,289, the entire contents of each of which are incorporated herein by reference.

Figure 15:
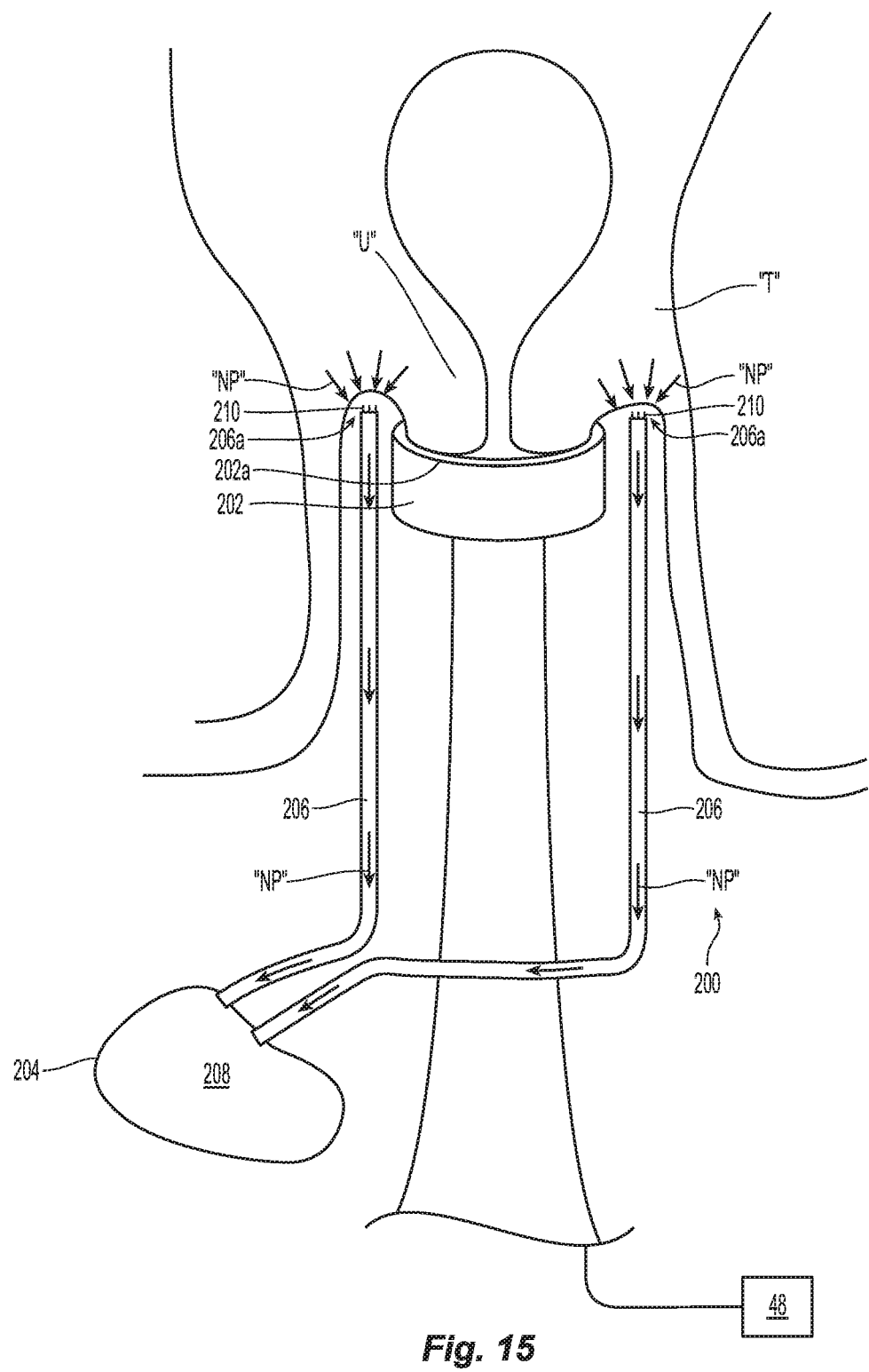
FIG. 15 is a schematic view of still another embodiment of a colpotomy system positioned in vivo.

With reference now to FIG. 15, one embodiment of a colpotomy system, generally referred to as colpotomy system 200, includes a colpotomy cup 202 and a vacuum assembly 204. Colpotomy cup 202 of colpotomy system 200 has an electrode 202a, such as a monopolar ring, secured to a distal end portion of colpotomy cup 202. Electrode 202a of colpotomy cup 202 is operatively coupled to electrosurgical energy source 48.

Vacuum assembly 204 of colpotomy system 200 includes one or more vacuum conduits 206 in fluid communication with a vacuum source 208 coupled to a proximal portion of vacuum conduits 206. Vacuum conduits 206 are positioned about colpotomy cup 202 and define distal openings 206a configured to enable vacuum source 208 to impart negative pressure "NP" on tissue "T," such as the uterus "U," to draw the uterus "U" down proximate electrode 202a of colpotomy cup 202. Vacuum conduits 206 may include one or more light emitting diodes 210 supported on a distal end portion of vacuum conduits 206. Light emitting diodes 210 are configured to emit light for facilitating positioning of colpotomy cup 202 adjacent the uterus "U." With the uterus "U" drawn proximate electrode 202a of colpotomy cup 202, electrode 202a can be activated by energy source 48 to effectuate a colpotomy. Although it may not be necessary to rotate electrode 202a to effectuate tissue "T" cutting and/or treating for performing a colpotomy, electrode 202a can be at least partially rotated, as desired, to facilitate cutting and/or treating of tissue "T."

Turning now to FIG. 16, another embodiment of a colpotomy system, generally referred to as colpotomy system 210, includes a colpotomy cup 212 and an electrode instrument 214. Electrode instrument 214 of colpotomy system 210 has a J-hook electrode 214a and a shaft 214b that supports J-hook electrode 214a on a distal end portion of shaft 214b. Electrode instrument 214 is electrically coupled to energy source 48. Colpotomy cup 212 defines an annular channel 212a in a distal end portion of colpotomy cup 212. Annular channel 212a, which may have a T-shape cross-section or the like, rotatably supports a rotatable sled 212b, which may include an I-shaped cross-section or the like.

Sled 212b of colpotomy cup 212 has a support flange 212c on a proximal end portion of sled 212b that rotatably secures sled 212b within channel 212a of colpotomy cup 212 and enables sled 212b to rotate relative to colpotomy cup 212, as indicated by arrows "K." Sled 212b further includes a plurality of circumferentially spaced-apart loops 212d that are each electrically coupled to energy source 48. Loops 212d may be disposed sub-flush from a distal surface of colpotomy cup 212 to enable clearance from tissue disposed above it and to facilitate easy hooking to electrode instrument 214.

Electrode instrument 214 may support a drive assembly 214c and an actuator 214d coupled to drive assembly 214c. Actuator 214d of electrode instrument 214 may be actuated to selectively adjust a length of J-hook electrode 214a of electrode instrument 214 relative to a distal end portion of shaft 214b of electrode instrument 214, as indicated by arrows "J" to facilitate coupling electrode instrument 214 to colpotomy cup 212 and/or to account for different tissue thickness.

In use, J-hook electrode 214a of electrode instrument 214 is hooked to one of loops 212d of sled 212b of colpotomy cup 212 so that electrosurgical energy can be conducted through J-hook electrode 214a of electrode instrument 214 and the respective loop 212d of colpotomy cup 212. As electrode instrument 214 is rotated about colpotomy cup 212, electrode instrument 214 rotates rotatable track 212b about colpotomy cup 212 so that a colpotomy can be effectuated as the electrosurgical energy is conducted through J-hook electrode 214a of electrode instrument 214 and the respective loop 212d of colpotomy cup 212.

As seen in FIG. 17, another embodiment of a colpotomy system, generally referred to as colpotomy system 216, includes a colpotomy cup 218 and electrode instrument 214 that are electrically coupled to energy source 48. While similar to colpotomy system 210, colpotomy cup 218 of colpotomy system 216 includes a rotatable sled 220 that forms a single loop 222. Colpotomy cup 218 may include one or more locating feature or indicia (e.g., markers, surface texture, etc.) to enable loop 222 to be quickly identified or located in vivo relative to colpotomy cup 218, for example, to illustrate where to effectuate a tissue cut-through.

Referring now to FIGS. 18A-18B, another embodiment of an electrode instrument, generally referred to as electrode instrument 224, includes a shaft assembly 226 and an electrode assembly 228. Shaft assembly 226 of electrode instrument 224 includes an outer shaft 226a and an inner shaft 226b that supports electrode assembly 228 of electrode instrument 224. Outer shaft 226a of shaft assembly 226 is axially movable relative to inner shaft 226b of shaft assembly 226 to selectively engage electrode assembly 228 of electrode instrument 224. Electrode assembly 228 includes a hook portion 228a and a clasp portion 228b.

Clasp portion 228b of electrode assembly 228 is movable relative (e.g., pivotably coupled) to inner shaft 226b of shaft assembly 226 between an open position (FIG. 18B), in which clasp portion 228b is spaced from hook portion 228a, and a closed position (FIG. 18A), in which clasp portion 228b is engaged with hook portion 228a to facilitate securement of electrode assembly 228 to an electrode of one of the presently disclosed colpotomy cups, such as loops 212d, 222 of colpotomy cups 212, 218 (FIGS. 16 and 17, respectively), for example.

Clasp portion 228b of electrode assembly 228 may be movable from the closed position to the open position in response to distal axial movement of outer shaft 226a of shaft assembly 226 relative to inner shaft 226b of shaft assembly 226, as illustrated by arrow "Q." Clasp portion 228b of electrode assembly 228 is positioned to move toward the closed position upon proximal axial movement of outer shaft 226a relative to inner shaft 226b of shaft assembly 226.

In some embodiments, clasp portion 228b of electrode assembly 228 may be spring biased by a spring (not shown) to enable clasp portion 228b to autonomously return to the closed position when outer shaft 226a is moved proximally relative to inner shaft 226b. In certain embodiments, the spring may be electrically insulated (e.g., includes dielectric material) to prevent electrical energy from being conducted through the spring. The spring may extend between hook and clasp portions 228a, 228b of electrode assembly 228.

Figure 19:
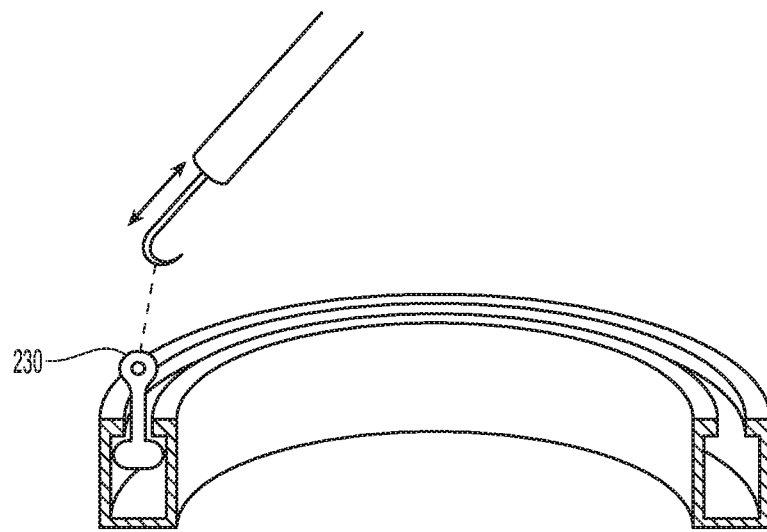
FIG. 19 is a perspective view, in partial cross-section, of a portion of still another embodiment of a colpotomy system.

With reference to FIG. 19, electrode sleds and/or loops, such as loops 212d, 222 (FIGS. 16 and 17) can extend distally beyond a distal surface of embodiments of the presently disclosed colpotomy cups, as illustrated by loop 230, to facilitate grasping/hooking and to improve visualization and/or location of loop 230.

Figure 20:
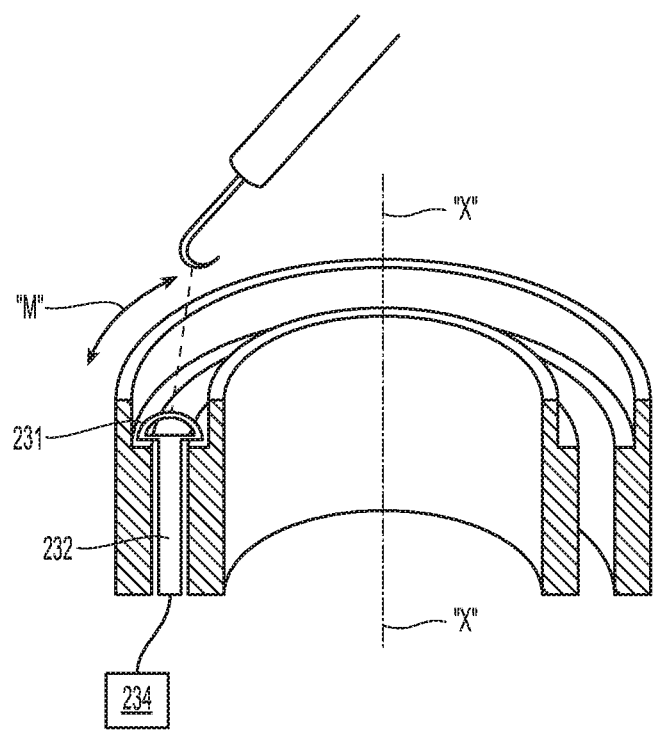
FIG. 20 is a perspective view, in partial cross-section, of a portion of yet another embodiment of a colpotomy system.
Figure 21:
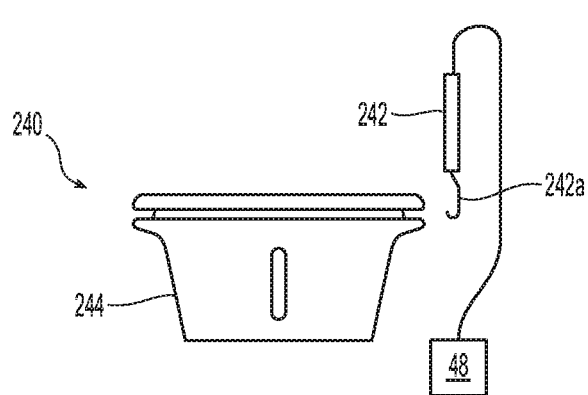
FIG. 21 is a side view of another embodiment of a colpotomy system.
Figure 22:
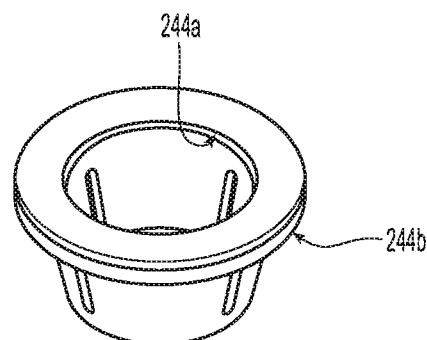
FIG. 22 is a perspective view of a colpotomy cup of the colpotomy system of FIG. 21.
Figure 23:
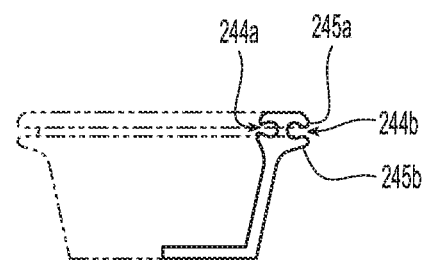
FIG. 23 is a side view of the colpotomy cup of FIG. 22 illustrating a profile thereof with portions of the colpotomy cup shown in phantom for clarity.

As seen in FIG. 20, any of the presently disclosed sleds and/or loops, such as loop 231, can be coupled to an internal shaft 232 supported within one of the presently disclosed colpotomy cups and/or uterine manipulators.

Internal shaft 232 can be driven rotationally about longitudinal axis "X-X," as indicated by arrows "M," via a drive assembly 234 that may be included with any of the presently disclosed uterine manipulators and/or colpotomy systems to enable external rotational control (e.g., by an actuator, such as a knob, on proximal portion, such as a handle of a uterine manipulator of this embodiment). Drive assembly 234 can include any suitable mechanical, electrical, and/or electro-mechanical component configured to manually and/or impart rotational force to internal shaft 232 (e.g., pneumatic, hydraulic, cables, rods, gears, pulleys, circuits, controllers, wiring, etc.) for rotating loop 231. In some embodiments, drive assembly 234 can be motorized.

Turning now to FIGS. 21-23 and FIGS. 24A and 24B, another embodiment of a colpotomy system, generally referred to as colpotomy system 240, includes an electrode instrument 242 and a colpotomy cup 244. Electrode instrument 242 of colpotomy system 240 includes a hook electrode 242a electrically coupled to energy source 48 to enable hook electrode 242a to conduct energy (e.g., monopolar). Colpotomy cup 244 of colpotomy system 240 defines an inner annular lip 244a and an outer annular lip 244b on a distal end portion of colpotomy cup 244. Each of inner and outer lips 244a, 244b of colpotomy cup 244 defines an annular channel 244c that is configured to receive hook electrode 242a of electrode instrument 242. Annular channels 224c of respective inner and outer lips 244a, 244b separate each of inner and outer lips 244a, 244b into an upper tier 245a and a lower tier 245b.

Figure 24A:
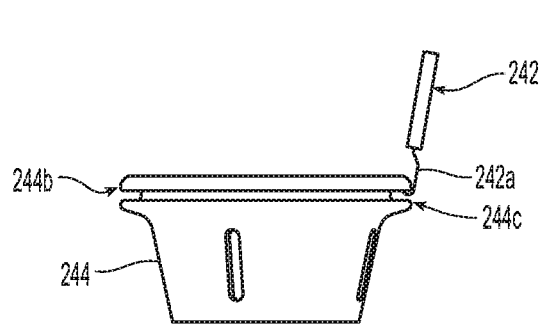
FIG. 24A is a side view of the colpotomy system of FIG. 21 with an electrode device thereof shown coupled to an outer lip of the colpotomy cup thereof.
Figure 24B:
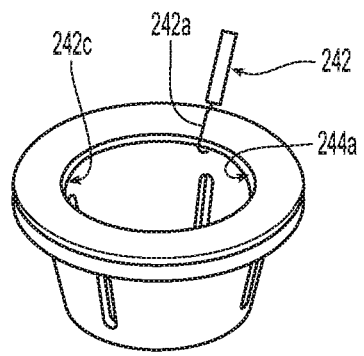
FIG. 24B is a perspective view of the colpotomy system of FIG. 21 with the electrode device thereof shown coupled to an inner lip of the colpotomy cup thereof.

As seen in FIGS. 24A and 24B, hook electrode 242a of electrode instrument 242 is selectively receivable by annular channels 244c of inner and/or outer annular lips 244a, 244b to guide hook electrode 242a circumferentially about colpotomy cup 244 to effectuate a colpotomy while hook electrode 242a of electrode instrument 242 conducts electrical energy.

Advantageously, inner and/or outer annular lips 244a, 244b provide a mechanical pairing that provides more accurate cuts and inhibits unsteady movement of electrode instrument 242 in vivo.

Securement of any of the components of the presently disclosed devices may be effectuated using known securement techniques such welding, crimping, gluing, fastening, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A colpotomy system, comprising:
   a colpotomy cup that extends to a distal surface and defines a longitudinal axis, the colpotomy cup having a first tube and a second tube, the first tube is an inner tube extending to a first distal end portion and defining a centerline, the second tube is an outer tube extending to a second distal end portion and defining a centerline, the centerlines of the first and second tubes being concentric with the longitudinal axis and the distal end portions of the respective first and second tubes being substantially longitudinally aligned, the inner tube includes an outer surface and an inner surface disposed radially inward of the outer surface; and
   a cutter operably coupled to the colpotomy cup and configured to travel along an arcuate path defined about the distal surface of the colpotomy cup, the cutter having a cutting surface positioned closer to the inner surface of the inner tube than the outer surface of the inner tube, the cutter actuatable to separate a uterus from a vagina as the cutter at least partially rotates about the longitudinal axis of the colpotomy cup.

2. The colpotomy system of claim 1, wherein the cutter is coupled to the first tube such that the cutter rotates with the first tube about the longitudinal axis and relative to the second tube.

3. The colpotomy system of claim 2, wherein the outer tube is positioned about the inner tube.

4. The colpotomy system of claim 1, wherein the cutting surface is configured to conduct energy therethrough.

5. The colpotomy system of claim 4, wherein the cutter is coupled to an electrosurgical energy source configured to transmit electrosurgical energy to the cutting surface, the cutting surface configured to conduct monopolar energy, bipolar energy, or combinations thereof.

6. The colpotomy system of claim 5, wherein the colpotomy cup includes a buffer that prevents the cutting surface from directly contacting tissue.

7. The colpotomy system of claim 1, wherein the cutter includes at least one light emitting diode configured to facilitate in vivo positioning of the cutter when illuminated.

8. The colpotomy system of claim 2, wherein the first tube includes a first treating surface and a second treating surface in opposed relation to the first treating surface, the first and second treating surfaces adapted to couple to an electrosurgical energy source and configured to treat tissue disposed between the first and second treating surfaces upon activation of the first and second treating surfaces.

9. The colpotomy system of claim 1, wherein the cutter includes a bipolar wheel configured to treat tissue.

10. The colpotomy system of claim 1, wherein the cutter includes first and second electrodes, the first electrode supported by a first material having a first magnetic polarity, the second electrode supported by a second material having a second magnetic polarity, the magnetic polarities of the first and second materials configured to maintain the first and second electrodes in opposing relation during cutting.

11. The colpotomy system of claim 10, wherein the first and second electrodes are bipolar and configured to sever tissue as the cutter encircles the distal surface of the colpotomy cup.

12. The colpotomy system of claim 1, further comprising a central shaft extending distally from the colpotomy cup and supporting an inflatable balloon, wherein the cutter includes a first electrode coupled to the distal surface of the colpotomy cup and a second electrode coupled to a proximal surface of the inflatable balloon, the inflatable balloon configured to maintain the first and second electrodes in relation during cutting.

13. A colpotomy system, comprising:
- a colpotomy cup that extends to a distal surface and defines a longitudinal axis, the colpotomy cup having a distal opening and movable between an unexpanded position and an expanded position to facilitate identification of the colpotomy cup in vivo, the colpotomy cup expanding radially outward to reduce a length of the colpotomy cup relative to the longitudinal axis thereof as the colpotomy cup moves from the unexpanded position to the expanded position; and
- a cutter operably coupled to the colpotomy cup and configured to travel along an arcuate path defined about the distal surface of the colpotomy cup, the cutter actuatable to separate a uterus from a vagina as the cutter at least partially rotates about the longitudinal axis of the colpotomy cup.

14. The colpotomy system of claim 1, wherein the cutter includes a movable blade that is actuatable to sever tissue as the cutter rotates about the longitudinal axis.

15. The colpotomy system of claim 1, wherein the colpotomy cup includes a plurality of light emitting diodes on the distal surface thereof.

16. The colpotomy system of claim 1, wherein the cutter is movable relative to the colpotomy cup between an undeployed position and a deployed position, the cutter including a cutting head that is recessed from the distal surface of the colpotomy cup in the undeployed position and that is extended above the distal surface of the colpotomy cup in the deployed position to enable the cutting head to sever tissue adjacent the distal surface of the colpotomy cup.

17. The colpotomy system of claim 16, wherein the cutter is in a form of a cautery spatula.

18. The colpotomy system of claim 1, further comprising a vacuum source and a plurality of vacuum conduits in fluid communication with the vacuum source, the vacuum conduits defined about the colpotomy cup and configured to apply negative pressure around the colpotomy cup to approximate tissue toward the distal surface of the colpotomy cup and to enable the cutter to sever tissue disposed in proximity to the distal surface of the colpotomy cup.

19. The colpotomy system of claim 1, further comprising a hooked electrode configured to operably couple to the colpotomy cup and adapted to couple to an electrosurgical energy source configured to transmit electrosurgical energy to the hooked electrode, the colpotomy cup including at least one loop configured to engage the hooked electrode, and wherein the hooked electrode is configured to rotate with the at least one loop around the longitudinal axis of the colpotomy cup relative to the distal surface of the colpotomy cup.

20. A colpotomy system, comprising:
- a colpotomy cup defining a longitudinal axis and defined by an inner lip, an outer lip, or combinations thereof, the colpotomy cup having a distal opening and movable between an unexpanded position and an expanded position to facilitate identification of the colpotomy cup in vivo, the colpotomy cup expanding radially outward to reduce a length of the colpotomy cup relative to the longitudinal axis thereof as the colpotomy cup moves from the unexpanded position to the expanded position; and
- a cutter operably coupled to the colpotomy cup and configured to travel along an arcuate path defined by the colpotomy cup, the cutter actuatable to separate a uterus from a vagina as the cutter at least partially rotates about the longitudinal axis of the colpotomy cup, the cutter including a hooked electrode, the hooked electrode configured to move relative to at least one of the inner lip, the outer lip, or combinations thereof, to sever tissue disposed about the colpotomy cup.

21. A colpotomy system, comprising:
- a colpotomy cup that extends to a distal surface and defines a longitudinal axis, the colpotomy cup having a first tube and a second tube, the first tube is an inner tube extending to a first distal end portion and defining a centerline, the second tube is an outer tube extending to a second distal end portion and defining a centerline, the centerlines of the first and second tubes being concentric with the longitudinal axis and the distal end portions of the respective first and second tubes being substantially longitudinally aligned, the inner tube includes an outer surface and an inner surface disposed radially inward of the outer surface; and
- a cutter operably coupled to the colpotomy cup and configured to travel along an arcuate path defined by the colpotomy cup, the cutter actuatable to separate a uterus from a vagina as the cutter at least partially rotates about the longitudinal axis of the colpotomy cup, the cutter including a hooked electrode, the hooked electrode being selectively movable to sever tissue disposed about the colpotomy cup.

* * * * *